United States Patent
Stadler et al.

(10) Patent No.: US 6,795,732 B2
(45) Date of Patent: Sep. 21, 2004

(54) IMPLANTABLE MEDICAL DEVICE EMPLOYING SONOMICROMETER OUTPUT SIGNALS FOR DETECTION AND MEASUREMENT OF CARDIAC MECHANICAL FUNCTION

(75) Inventors: Robert W. Stadler, Shoreview, MN (US); William J. Combs, Minnetonka, MN (US); David Lipson, North Andover, MA (US)

(73) Assignee: Medtronic, Inc., Minneapolis, MN (US)

( * ) Notice: Subject to any disclaimer, the term of this patent is extended or adjusted under 35 U.S.C. 154(b) by 294 days.

(21) Appl. No.: 10/002,338

(22) Filed: Oct. 30, 2001

(65) Prior Publication Data

US 2003/0083702 A1 May 1, 2003

(51) Int. Cl.[7] .................. A61N 1/365; A61B 5/107; A61B 5/103
(52) U.S. Cl. .................. 607/17; 607/18; 600/513; 600/515
(58) Field of Search .................. 607/4–6, 9, 17, 607/18; 600/508–509, 513, 515

(56) References Cited

U.S. PATENT DOCUMENTS

| | | | |
|---|---|---|---|
| 3,937,226 A | 2/1976 | Funke | 128/419 |
| 4,088,140 A | 5/1978 | Rockland et al. | 128/419 |
| 4,109,644 A | 8/1978 | Kojima | 128/2 |
| 4,332,259 A | 6/1982 | McCorkle, Jr. | 128/786 |
| 4,354,497 A | 10/1982 | Kahn | 128/419 |
| 4,354,502 A | 10/1982 | Colley et al. | 128/663 |
| 4,458,677 A | 7/1984 | McCorkle, Jr. | 128/786 |
| 4,548,203 A | 10/1985 | Tacker, Jr. et al. | 128/419 |
| 4,802,490 A | 2/1989 | Johnston | 128/661.08 |
| 4,928,688 A | 5/1990 | Mower | 128/419 |
| 4,936,304 A | 6/1990 | Kresh et al. | 607/23 |

(List continued on next page.)

FOREIGN PATENT DOCUMENTS

| | | | |
|---|---|---|---|
| EP | 0467695 A2 | 7/1991 | A61N/1/362 |
| EP | 0536873 A1 | 7/1992 | A61N/1/39 |
| EP | 1129736 A1 | 2/2001 | A61N/1/10 |
| WO | WO 98/46140 | 10/1998 | A61B/8/00 |
| WO | WO 00/69490 | 11/2000 | A61M/1/10 |
| WO | WO 00/78375 A1 | 12/2000 | A61N/1/12 |

OTHER PUBLICATIONS

Cazeau et al., Four Chamber Pacing in Dilated Cardiomyopathy, Nov. 1994, Part II PACE vol. 17, pp. 1974–1979.
Daubert et al., Permanent Left Ventricular Pacing with Transvenous Leads Inserted Into the Coronary Veins, Jan. 1998, Part II, PACE vol. 21, pp. 239–245.

(List continued on next page.)

Primary Examiner—Carl H. Layno
(74) Attorney, Agent, or Firm—Michael C. Soldner; Girma Wolde-Michael

(57) ABSTRACT

Implantable medical devices (IMDs) for detection and measurement of cardiac mechanical and electrical function employ a system and method for determining mechanical heart function and measuring mechanical heart performance of upper and lower and left and right heart chambers without intruding into a left heart chamber through use of a dimension sensor. The dimension sensor or sensors comprise at least a first sonomicrometer piezoelectric crystal mounted to a first lead body implanted into or in relation to one heart chamber that operates as an ultrasound transmitter when a drive signal is applied to it and at least one second sonomicrometer crystal mounted to a second lead body implanted into or in relation to a second heart chamber that operates as an ultrasound receiver.

56 Claims, 19 Drawing Sheets

U.S. PATENT DOCUMENTS

| | | | |
|---|---|---|---|
| 5,091,404 A | 2/1992 | Elgebaly | 514/401 |
| 5,139,020 A | 8/1992 | Koestner et al. | 128/419 |
| 5,156,154 A | 10/1992 | Valenta, Jr. et al. | 128/661.09 |
| 5,156,157 A | 10/1992 | Valenta, Jr. et al. | 128/662.06 |
| 5,161,540 A | 11/1992 | Mueller | 128/695 |
| 5,174,289 A | 12/1992 | Cohen | 128/419 |
| 5,183,040 A | 2/1993 | Nappholz et al. | 128/419 |
| 5,188,106 A | 2/1993 | Nappholz et al. | 128/419 |
| 5,199,106 A | 3/1993 | Bourke et al. | 395/275 |
| 5,243,976 A | 9/1993 | Ferek-Petric et al. | 607/6 |
| 5,267,560 A | 12/1993 | Cohen | 607/25 |
| 5,305,745 A | 4/1994 | Zacouto | 600/324 |
| 5,316,001 A | 5/1994 | Ferek-Petric et al. | 128/661.08 |
| 5,403,356 A | 4/1995 | Hill et al. | 607/14 |
| 5,514,161 A | 5/1996 | Limousin | 607/9 |
| 5,515,853 A | 5/1996 | Smith et al. | 128/661.01 |
| 5,544,656 A | 8/1996 | Pitsillides et al. | 128/661.04 |
| 5,553,611 A * | 9/1996 | Budd et al. | 600/374 |
| 5,564,434 A | 10/1996 | Halperin et al. | 128/748 |
| 5,584,867 A | 12/1996 | Limousin et al. | 607/9 |
| 5,603,327 A | 2/1997 | Eberle et al. | 128/662.06 |
| 5,674,259 A | 10/1997 | Gray | 607/20 |
| 5,720,768 A | 2/1998 | Verboven-Nelissen | 607/9 |
| 5,779,638 A | 7/1998 | Vesely et al. | 600/437 |
| 5,792,203 A | 8/1998 | Schroeppel | 607/30 |
| 5,795,298 A | 8/1998 | Vesely et al. | 600/450 |
| 5,797,970 A | 8/1998 | Pouvreau | 607/9 |
| 5,817,022 A | 10/1998 | Vesely | 600/443 |
| 5,830,144 A | 11/1998 | Vesely | 600/459 |
| 5,902,324 A | 5/1999 | Thompson et al. | 607/9 |
| 6,070,100 A | 5/2000 | Bakels et al. | 607/9 |
| 6,219,579 B1 | 4/2001 | Bakels et al. | 607/17 |
| 6,223,082 B1 | 4/2001 | Bakels et al. | 607/17 |
| 6,298,269 B1 | 10/2001 | Sweeney | 607/28 |
| 6,406,422 B1 * | 6/2002 | Landesberg | 600/17 |
| 6,511,413 B2 * | 1/2003 | Landesberg | 600/17 |
| 6,540,699 B1 * | 4/2003 | Smith | 600/587 |

OTHER PUBLICATIONS

Lee et al., Miniature Implantable Sonomicrometer System, Jan. 1970, Journal of Applied Physiology, vol. 28, No. 1, pp. 110–112.

Daubert et al., Permanent Dual Atrium Pacing in Major Interatrial Conduction Blocks: A Four Year Experience, Apr. 1993, Part II PACE, vol. 16, p 885.

Daubert et al., Renewal of Permanent Left Atrial Pacing Via the Coronary Sinus, Apr. 1992, Part II, PACE, vol. 15, pp. 572.

* cited by examiner

IMPLANTABLE MEDICAL DEVICE EMPLOYING SONOMICROMETER OUTPUT SIGNALS FOR DETECTION AND MEASUREMENT OF CARDIAC MECHANICAL FUNCTION

CROSS-REFERENCE TO RELATED APPLICATION

Reference is hereby made to commonly assigned, co-pending U.S. patent application Ser. No. 10/000,973 filed on even date herewith entitled IMPLANTABLE MEDICAL DEVICE FOR MONITORING CARDIAC BLOOD PRESSURE AND CHAMBER DIMENSION in the names of Lawrence J. Mulligan et al.

FIELD OF THE INVENTION

The present invention relates generally to implantable medical devices (IMDs) that deliver therapies to the heart and/or monitor cardiac physiologic parameters that, in particular, involves implantation of sonomicrometer piezoelectric crystals in or in relation to the heart chambers to detect occurrence of and magnitudes of the mechanical movements of the heart chambers.

BACKGROUND OF THE INVENTION

A wide variety of IMDs have been developed over the years or are proposed that provide cardiac rhythm management of disease states manifested by cardiac rhythm disorders and heart failure. Implantable pacemakers have been developed that monitor and restore heart rate and rhythm of hearts that suffer bradycardia (too-slow or irregular heart rate), tachycardia (regular but excessive heart rate) and heart failure (the inability of the heart to maintain its workload of pumping blood to the body). Implantable cardioverter-defibrillators (ICDs) have been developed that deliver programmed cardioversion/defibrillation energy level shocks to the atria in response to detection of atrial fibrillation (rapid, uncontrolled heartbeats in the atria) or to the ventricles in response to life-threatening, ventricular tachyarrhythmias. Typically, single and dual chamber bradycardia pacing systems are also incorporated into ICDs. Implantable diagnostic and monitoring systems are targeted for an emerging field that may change the way medicine is practiced. These systems typically monitor patients in their home environments, providing treating physicians with more complete information about their patients changing cardiac conditions. Proposals have been made to incorporate capabilities of pervasive computing into such therapy delivery and monitoring IMDs and the external medical devices employed to communicate with the Ms and remote locations via the worldwide web.

These cardiac IMDs have traditionally employed capabilities of sensing the electrogram of the heart manifested by the cyclic PQRST waveform at one or more location principally to detect the contraction of the atria as evidenced by a P-wave meeting P-wave detection criteria of an atrial sense amplifier and/or the contraction of the ventricles as evidenced by an R-wave meeting R-wave detection criteria of a ventricular sense amplifier. The timing of detected atrial and ventricular sense events is used to ascertain normal sinus rhythm or the presence of bradycardia, tachycardia or tachyarrhythmia in the monitoring and therapy delivery contexts.

Among the earliest developed cardiac rhythm management IMDs were simple, single chamber, fixed rate pacing systems comprising an implantable pulse generator (IPG) and a lead bearing one or more pace/sense electrode adapted to be placed in contact with the heart chamber to be paced (commonly referred to as pacemakers) that provided fixed rate pacing to a single heart chamber when the heart rate fell below a lower rate limit. The earliest ICDs delivered a defibrillation shock to the ventricles when heart rate and regularity or morphology criteria were met. It was proposed that blood pressure sensors or accelerometers be incorporated so that the absence of mechanical heart function during fibrillation could also be detected to confirm the tentative determination of fibrillation before a shock therapy was delivered, but suitable sensors were not available.

Over the years, such pacemakers and ICDs evolved in complexity and capabilities as described in greater detail herein. Increasingly complex signal processing algorithms were developed and implemented in the effort to glean as much information as possible about the instantaneous state of the heart in order to provide the appropriate therapy to restore heart rhythm and to avoid mis-delivery of a therapy that would potentially harm the patient.

The accuracy of detection of atrial and ventricular sense events by sense amplifiers can deteriorate due to a wide variety of effects that distort the signal applied to the sense amplifiers such that the P-wave or R-wave is either not detected (an "undersensing" condition) or an atrial or ventricular sense event is mistakenly declared (an "oversensing" condition). The ability to distinguish a true sense event in a distorted signal is also complicated by the necessity of protecting sense amplifier circuitry following delivery of a pacing pulse or cardioversion/defibrillation shock. Conventionally, the sense amplifier circuits are disconnected from the sense electrodes during a blanking time period timed out following delivery of a pacing pulse or cardioversion/defibrillation shock to protect the circuitry. Longer refractory time periods are also timed out following delivery of a pacing pulse or cardioversion/defibrillation shock during which any sense event is declared to be refractory to avoid inappropriately restarting timing periods.

It has been recognized that other indicators of heart function, particularly indicators related to mechanical heart function, would be of great value in augmenting the algorithms that process atrial and ventricular sense events in order to resolve ambiguities that can inherently arise. It is also desirable to be able to ascertain whether a delivered pacing pulse has "captured" the heart, i.e., caused the heart chamber to contract. Further more, it is desirable to be able to rapidly determine that a delivered cardioversion/defibrillation shock has effectively terminated a tachyarrhythmia and that the heart has returned to normal sinus rhythm.

There are other situations where indicators related to mechanical heart function incorporated into pacing systems would be useful. Patients suffering from chronic heart failure or congestive heart failure (CHF) manifest an elevation of left ventricular end-diastolic pressure, according to the well-known heterometric autoregulation principles espoused by Frank and Starling. This may occur while left ventricular end-diastolic volume remains normal due to a decrease in left ventricular compliance concomitant with increased ventricular wall stiffness. CHF due to chronic hypertension, ischemia, infarct or idiopathic cardiomyopathy is associated with compromised systolic and diastolic function involving decreased atrial and ventricular muscle compliance. These may be conditions associated with chronic disease processes or complications from cardiac surgery with or without specific disease processes. Most heart failure patients suffer from symptoms which may include a general weakening of the contractile function of the cardiac muscle, attendant enlargement thereof, impaired myocardial relaxation and depressed ventricular filling characteristics in the diastolic phase following contraction. Pulmonary edema, shortness of breath, and disruption in systemic blood pressure are associated with acute exacerbations of heart failure.

These disease processes lead to insufficient cardiac output to sustain mild or moderate levels of exercise and proper function of other body organs, and progressive worsening eventually results in cardiogenic shock, arrhythmias, electromechanical dissociation, and death. In order to monitor the progression of the disease and to assess efficacy of prescribed treatment, it is necessary to obtain accurate measures of the heart geometry, the degree of heart enlargement, and the mechanical pumping capability of the heart, e.g., ejection fraction, under a variety of metabolic conditions the patient is likely to encounter on a daily basis. These parameters are typically measured through the use of external echocardiogram equipment in the clinical setting. However, the measurement procedure is time consuming to perform for even a resting patient and cannot be practically performed replicating a range of metabolic conditions. Typically, the echocardiography procedure is performed infrequently and months or years may lapse between successive tests, resulting in a poor understanding of the progress of the disease or whether or not intervening drug therapies have been efficacious. Quite often, only anecdotal evidence from the patient is available to gauge the efficacy of the prescribed treatment.

For these and other reasons, it has been proposed to employ sensors typically located in a blood vessel or heart chamber that respond to mechanical heart function to derive a metric that changes in value over the heart cycle in proportion to the strength, velocity or range of motion of one or more of the heart chambers or valves. It is desirable that such a metric would complement the measurement of the EGM to more confidently detect an arrhythmia or trigger delivery of a delivered therapy and to derive a number of indicators of intrinsic cardiac performance and response to a delivered therapy that can be employed to confirm or alter delivery of the therapy or indicate the state and progress of the underlying cardiac disease.

Thus, permanently implantable sensors have been proposed and used to some extent to measure blood pressure, temperature, concentrations of various blood gases, and/or blood flow as blood fills and is ejected from a heart chamber of interest. A lead of the type described in commonly assigned U.S. Pat. No. 5,564,434 possesses capacitive blood pressure and temperature sensors as well as EGM sense electrodes that can be employed in this manner. Doppler flow sensors have also been proposed.

It has been proposed to employ permanently implantable sensors that provide a more direct measure of mechanical motion of muscle mass or particular structures of the heart, including one or more of valve opening and closing and the motion or expansion and contraction of the septal wall and the ventricular and atrial wall. Such sensors include intracardiac pressure sensors, accelerometers, impedance measurement electrode systems and Doppler motion sensors. In an approach related to monitoring rejection of heart transplants, a magnetic field responsive Hall effect device and a permanent magnet are implanted directly across the septum or a heart wall as taught in U.S. Pat. No. 5,161,540, and the Hall effect device is powered by an implantable generator and telemetry transceiver. The compliance of the heart wall is monitored to detect any loss of compliance characteristic of rejection of the heart transplant.

As noted in U.S. Pat. No. 5,544,656, measurement of myocardial wall thickness, as well as end-systolic and end-diastolic dimensions, are important in evaluating the effects of changes in regional myocardial function and contractility, including evaluating myocardial oxygen supply and demand, in acute and chronic animal studies. A transit-time sonomicrometry system is disclosed in the background of '656 patent that uses two piezoelectric crystals, one as a transmitter and the other as a receiver, and operates by measuring the time required for ultrasound to travel between the transmitting and receiving transducers. An advantage of this system is its ability to provide an absolute dimension signal output calibrated in units of distance. However, it is asserted that the two-crystal system has several disadvantages such as (1) it is necessary to insert a piezoelectric crystal through the myocardium, which can damage the myocardial nerve and blood vessel supply of the myocardial wall, (2) it is difficult to position precisely the endocardial crystal at the tissue/blood sub-endocardial interface, and (3) it can be difficult to maintain good alignment at all times throughout the cardiac cycle for short term and particularly during longer duration studies (>12 weeks). Tracking and non-tracking Doppler echo displacement systems and their purported deficiencies are also disclosed in the '656 patent.

The '656 patent then discloses a closed-loop, single-crystal, ultrasonic sonomicrometer capable of identifying the myocardial muscle/blood interface and continuously tracking this interface throughout the cardiac cycle using a unique piezoelectric transducer that operates in the manner of a Doppler echo sensor implanted at least partly in the myocardium and partly in the blood within a heart chamber. The echo sensing transducer disclosed in the '656 patent is characterized as overcoming these deficiencies in measuring myocardial wall thickness noted with transit-time sonomicrometry system and the tracking and non-tracking Doppler echo displacement systems. PCT publication WO 99/07285 also discloses an ultrasound echocardiography system particularly to measure the left ventricular performance using an array of ultrasonic crystals on a lead implanted in the right ventricle and aimed toward the ventricular septum and the left ventricular wall. T Sonomicrometer systems that are installed epicardially about the heart to measure heart movement across a number of vectors are also disclosed in the article "Miniature Implantable Sonomicrometer System", by Robert D. Lee et al., (*Journal of Applied Physiology*, Vol. 28, No. 1, January 1970, pp. 110–112), in EP0 467 695 A2, and in PCT publication WO 00/69490. The Lee article describes an implantable monitoring system attached to the epicardial electrodes. But, it is necessary to perform invasive surgery to expose the locations where sonomicrometer crystals are surgically attached to the epicardium.

Some of the various chronically implanted sensors described above are intended to be incorporated into lead bodies that are typically introduced transveniously into the relatively low pressure right heart chamber or blood vessels accessible from the right atrium through the patient's venous system. The introduction of such sensors into left heart chambers through the arterial system introduces complications that may be difficult to manage both acutely and chronically. The surgical approach to the exterior of the heart is also not favored as it complicates the surgery and recovery of the patient. However, measurement of left heart function is desirable in a number of clinical cases including chronic heart failure.

Moreover, despite many years of development and numerous proposals of various types of mechanical heart function or performance measuring sensors, there remains a need for suitable sensors located in a blood vessel or right heart chamber that responds to mechanical heart function to derive a metric that changes in value over the heart cycle in proportion to the strength, velocity or range of motion of one or more of the heart chambers or valves. The prior mechanical heart function sensors devices have been generally unsuccessful due to a.) the added complexity and reduced reliability of associated leads, and b.) the challenge of obtaining useful hemodynamic information from such surrogate measurements, which usually address only the right heart chambers. There remains a need for derivation of such mechanical heart metrics would complement the measurement of the EGM to more confidently monitor heart failure or myocardial infarction, detect an arrhythmia or trigger delivery of a delivered therapy and to derive a number of indicators of intrinsic cardiac performance and response to a delivered therapy that can be employed to confirm or alter delivery of the therapy or indicate the state and progress of the underlying cardiac disease.

SUMMARY OF THE INVENTION

In view of the above need, the present invention provides a system and method incorporated into therapy delivery and/or monitor IMDs employing dimension sensors for determining mechanical heart function and measuring mechanical heart performance of both left and right heart chambers without intruding into a left heart chamber or requiring invasive surgery to access the left heat chamber epicardium.

The dimension sensors comprise at least a first sonomicrometer piezoelectric crystal mounted to a first lead body implanted into or in relation to one heart chamber, e.g., the RV, that operates as an ultrasound transmitter when a drive signal is applied to it or as an ultrasound receiver and at least one second sonomicrometer crystal mounted to a second lead body implanted into or in relation to a second heart chamber e.g., the left ventricle (LV), the left atrium (LA) or the right atrium (RA), that operates as an ultrasound receiver or as an ultrasound transmitter when a drive signal is applied to it, respectively. The ultrasound receiver converts impinging ultrasound energy transmitted from the ultrasound transmitter through blood and heart tissue into an electrical signal. The time delay between the generation of the transmitted ultrasound signal and the reception of the ultrasound wave varies as a function of distance between the ultrasound transmitter and receiver which in turn varies with contraction and expansion of a heart chamber between the first and second sonomicrometer crystals. One or more additional sonomicrometer piezoelectric crystal can be mounted to additional lead bodies, such that the distances between the three or more sonomicrometer crystals can be determined. In each case, the sonomicrometer crystals are distributed about a heart chamber of interest such that the distance between the separated ultrasound transmitter and receiver crystal pairs changes with contraction and relaxation of the heart chamber.

The RV-LV distance between the RV and LV crystals is a measure of LV dimension, and changes in the LV dimension over the cardiac cycle are strongly correlated with changes in LV volume as the LV fills during diastole and empties during systole. The LV-RA distance between the LV and RA crystals varies as a function of RA mechanical activity as the RA fills and empties in a pattern during normal sinus rhythm that markedly differs from the pattern exhibited during atrial fibrillation and other forms of ineffective atrial contraction. The RV-RA distance and RV-LA distance between the RV sonomicrometer crystal and the respective RA and LA sonomicrometer crystals varies as a function of a mixture of atrial and ventricular activity.

The invention thus involves the incorporation of sonomicrometer piezoelectric crystals into cardiac leads, the distribution of the sonomicrometer piezoelectric crystals about the heart chambers and the incorporation of a control and measurement system in the operating system of the IMD that measures the distance between the sonomicrometer crystals as the heart expands and contracts over each heart cycle. In one embodiment, first and second cardiac pacing leads or cardioversion/defibrillation leads bearing first and second sonomicrometer crystals, respectively, are implanted through the coronary sinus (CS) and into the great cardiac vein along the LV and in the RV apex, respectively. Preferably, a third cardiac pacing lead or cardioversion/defibrillation lead bearing a third sonomicrometer crystal is implanted in the RA appendage. The lead conductors are coupled to emission, reception and dimension measurement circuitry within an IMD IPG or monitor that drives one selected piezoelectric crystal as an emitter or generator and the other piezoelectric crystals as receivers, whereby the distances between the crystal pairs can be measured as a function of the measured transit time for the transmitted signal to be received by multiplying the time of travel by the speed of sound in the tissue.

The invention also includes the incorporation of the sonomicrometer crystal into a pacing lead with two or more conductors, such that the crystal is wired in parallel with two of the conductors in the lead. For example, a crystal could be wired in parallel with the ring and tip pace/sense electrodes of a pacing lead. The ultrasound crystal has very low impedance to signals near its resonance frequency (near 1 MHz) and very high impedance to lower frequency signals. Pacing pulses, which contain lower frequencies, would preferentially be delivered to the tissue via the tip and ring electrodes, whereas high frequency pulses to excite the ultrasound crystal would be preferentially delivered to the crystal. The low pass filter of the pacing sense amplifier does not pass the very high frequency ultrasound signals. Thus, the sonomicrometer function does not interfere with normal pacing and sensing functions. As an alternative implementation, the pacing pulse could be delivered simultaneously to the tip and ring pace/sense electrodes, with the IPG case or can as an anode, thereby delivering an effective pacing pulse without any energy dissipation through the ultrasound crystal. As a second alternative, filtering circuitry could be incorporated into the lead to ensure delivery of pacing pulses to the pace/sense electrodes and ultrasound pulses to the crystals.

A principal advantage of the system and method of the present invention include the ability to directly monitor left ventricular function without entering the left side of the heart, the ability to monitoring atrial mechanical function, and the potential for parallel wiring with pace/sense electrodes, thereby avoiding the need for additional conductors within the lead body and connector elements.

The system and method of the present invention is advantageously employed to measure cardiac dimensions in real time and to either record or transmit these values for monitoring purposes or to use these values as feedback to modify the delivery of electrical or pharmacological therapy, particularly in the treatment of heart failure.

The system and method of the present invention can be advantageously employed in the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive anti-tachyarrhythmia therapies, or determining the need to compensate for a weakly beating heart after therapy delivery, and the like.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail herein in the context of an AV sequential, three chamber or four chamber, pacing system operating in demand, atrial tracking, and triggered pacing modes for restoring synchrony in depolarizations and contraction of left and right ventricles in synchronization with atrial sensed and paced events for treating heart failure and/or bradycardia in those chambers. This embodiment of the invention is programmable to operate as a three or four chamber pacing system having art AV synchronous operating mode for restoring upper and lower heart chamber synchronization and right and left atrial and/or ventricular chamber depolarization synchrony.

It should be appreciated that the present invention may be utilized in an implantable monitor to gather data in patients suffering various forms of heart failure. The system of the present invention can also may be incorporated into an anti-tachyarrhythmia system including specific high rate pacing and cardioversion shock therapies of typical ICDs for providing staged therapies to treat a diagnosed tachyarrhythmia and optionally including any of the described bradycardia pacing systems.

It will be therefore understood that the various uses of the dimension signals derived employing the sonomicrometry system of the present invention described herein can be employed separately or in various combinations in these complex multi-site monitoring, pacing and/or ICD systems and can alternatively be used in simpler dual chamber and single chamber pacemakers, monitors and ICDs which can constitute sub-sets of the components of this illustrated embodiment of the invention.

Figure 1:
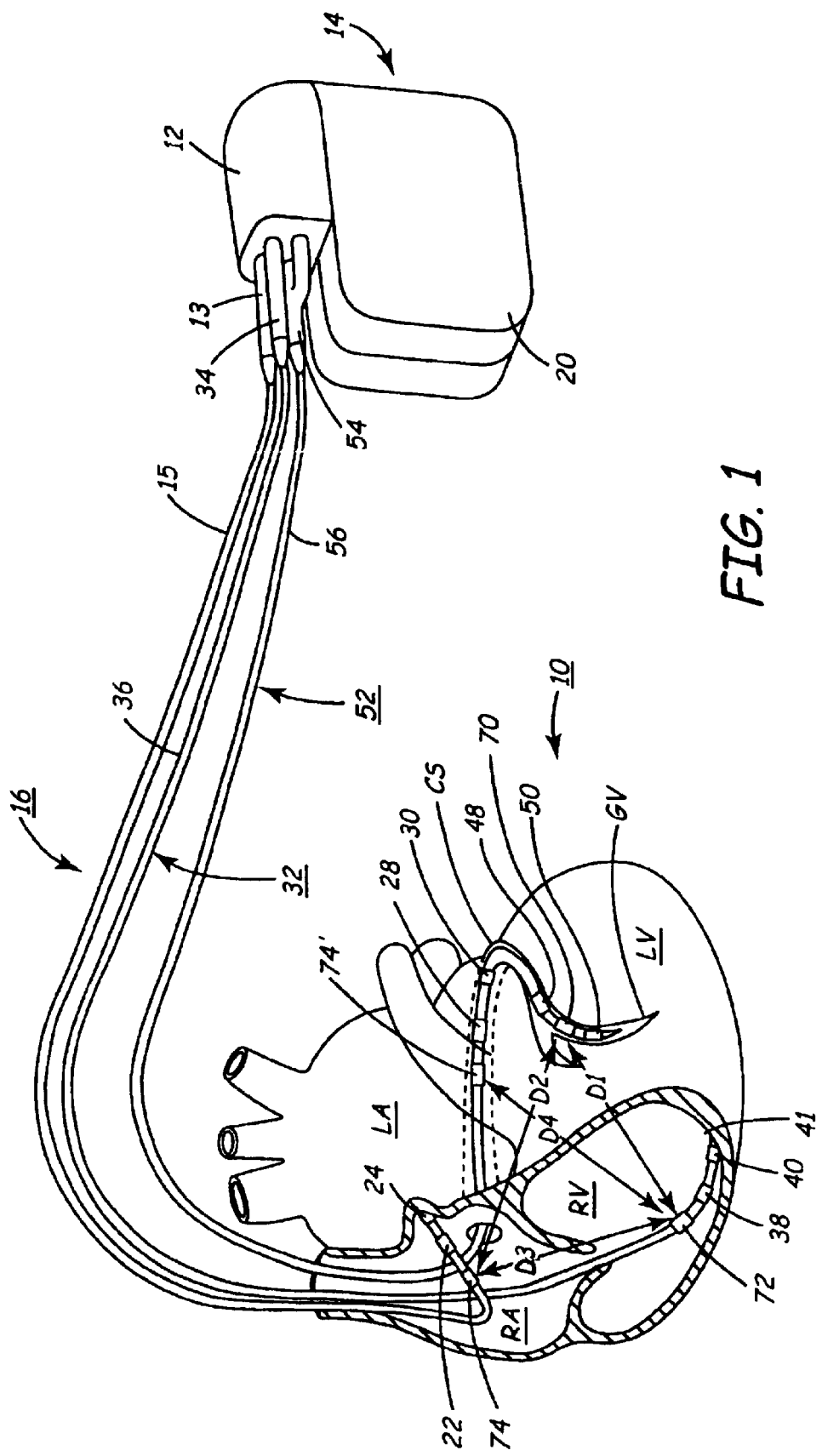
FIG. 1 is a schematic diagram depicting a multi-channel, atrial and bi-ventricular, monitoring/IPG IMD in which the present invention is preferably implemented employing distributed sonomicrometer piezoelectric crystals to derive dimension signals during systolic and diastolic heart contraction phases.

In FIG. 1, heart 10 includes the upper heart chambers, the RA and LA, and the lower heart chambers, the RV and left ventricle LV and the various blood vessels attached thereto. The coronary sinus (CS) extends from the opening in the RA laterally around the LA and LV wall to form the great vein (GV) that extends further inferiorly into branches of the GV. FIG. 1 also shows a schematic representation of an implanted, three or four chamber cardiac pacemaker or monitor or ICD of the above noted types for restoring AV synchronous contractions of the atrial and ventricular chambers and simultaneous or sequential pacing of the right and left ventricles, and/or for monitoring the mechanical function of one or more heart chamber and/or delivering anti-tachyarrhythmia therapies to counter detected malignant tachyarrhythmias. For simplicity of explanation, the preferred embodiments herein will be described in the context of an IMD providing therapy delivery and monitoring capabilities, but it will be understood that the present invention can be implemented simply in a monitor that monitors mechanical heart function.

The pacemaker or ICD IPG 14 depicted in FIG. 1 is implanted subcutaneously in a patient's body between the skin and the ribs. Three endocardial leads 16, 32 and 52 connect the IPG 14 with the RA, the RV and both the LA and the LV, respectively. Each lead has two electrical conductors and at least one pace/sense electrode, and a remote indifferent can electrode 20 is formed as part of the outer surface of the housing of the IPG 14. The pace/sense electrodes and the remote indifferent can electrode 20 (IND_CAN electrode) can be selectively employed to provide a number of unipolar pace/sense electrode combinations for pacing and sensing functions, particularly sensing far field signals, e.g. a far field R-wave (FFRS), or bipolar pace/sense electrodes. The depicted positions in or about the right and left heart chambers are also merely exemplary. Moreover, in the practice of certain of the embodiments of the invention described below, other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through the superior vena cava (SVC) and into the RA of the heart 10, and the distal end of the RA lead 16 is attached to the RA wall within RA appendage the by an attachment mechanism 24 that can form one pace/sense electrode. The bipolar endocardial RA lead 16 is formed with an in-line connector 13 fitting into a bipolar bore of IPG connector block 12. The in-line connector 13 is coupled to an RA lead conductor pair within lead body 15 and connected with distal tip RA pace/sense electrode 24 and a proximal ring-shaped RA pace/sense electrode 22. Delivery of RA pace pulses and sensing of the RA EGM and RA sense events are effected between the distal tip RA pace/sense electrode 24 and proximal ring-shaped RA pace/sense electrode 22, wherein the proximal ring-shaped RA pace/sense electrode 22 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 24 and proximal ring-shaped RA pace/sense electrode 22 can be employed with the IND_CAN electrode 20 for unipolar RA pacing and/or sensing. It will be understood in the ICD embodiment that the RA lead 16 can also include an elongated RA/SVC cardioversion/defibrillation electrode and associated conductor and connector element.

The depicted bipolar endocardial RV lead 32 is transvenously advanced through the SVC and the RA and into the RV where its distal tip RV pace/sense electrode 40 is fixed in place in the apex by a conventional distal attachment mechanism 41 (which may also constitute the distal tip pace/sense electrode). The RV lead 32 is formed with an RV lead conductor pair within lead body 36 extending from an in-line connector 34 fitting into a bipolar bore of IPG connector block 12. A first conductor or the RV lead conductor pair is connected with distal tip RV pace/sense electrode 40, and a second conductor of the RV lead conductor pair is connected with the ring-shaped RV pace/sense electrode 38. Delivery of RV pace pulses and sensing of RV EGM and RV sense events are effected between the distal tip RV pace/sense electrode 40 and the proximal ring-shaped RV pace/sense electrode 38, wherein the proximal ring-shaped RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring-shaped RV pace/sense electrode 38 can be employed with the IND_CAN electrode 20 for unipolar RV pacing and/or sensing. It will be understood in the ICD embodiment that the RV lead 32 can also include an elongated RV cardioversion/defibrillation electrode and associated conductor and connector element.

In this illustrated embodiment, a multi-polar, endocardial CS lead 52 is advanced through the SVC, the RA, the ostium of the CS, the CS itself, and into the GV or a further cardiac vessel branching from it. A pair of distal, ring-shaped, LV/CS pace/sense electrodes 48 and 50 are thus located deep in the GV alongside the LV to allow the depolarization of the LV to be detected and to allow pacing pulses to be delivered to the LV simultaneously with or in timed relation with the delivery of pacing pulses of the RV. In the illustrated four chamber or channel embodiment, LV/CS lead 52 also bears proximal, ring-shaped, LA/CS pace/sense electrodes 28 and 30 positioned along the CS lead body 56 to lie in the larger diameter CS adjacent the LA.

The LV/CS lead 52 is formed with a multiple conductor lead body 56 coupled at the proximal end connector 54 fitting into a bore of IPG connector block 12. In this case, the CS lead body 56 would encase electrically insulated LV and LA lead conductor pairs extending distally from connector elements of a dual bipolar connector 54. The LA lead conductor pair extends proximally from the more proximal LA/CS pace/sense electrodes 28 and 30, and the LV lead conductor pair extends proximally from the more distal LV/CS pace/sense electrodes 48 and 50. A small diameter lead body 56 is selected in order to lodge the distal LV/CS pace/sense electrode 50 deeply in a vein branching inferiorly from the great vein GV. It will be understood that LV/CS lead 52 could bear a single LA/CS pace/sense electrode 28 and/or a single LV/CS pace/sense electrode 50 that are paired with the IND_CAN electrode 20 or one of the ring-shaped pace/sense electrodes 22 or 38 for pacing and sensing in the LA and LV, respectively. Typically, such a CS lead 52 (as well as CS leads bearing only LA/CS or LV/CS pace/sense electrodes) as well as CS cardioversion/defibrillation leads do not employ any fixation mechanism and instead rely on the close confinement within these vessels to maintain the pace/sense electrode or electrodes or cardioversion/defibrillation electrode at a desired site. It will be understood in the ICD embodiment that the CS lead 52 can also include an elongated CS/LV cardioversion/defibrillation electrode and associated conductor and connector element.

In accordance with one preferred embodiment of the present invention, a sonomicrometer crystal 70 is incorporated within a distal segment of the lead body 56 of LV/CS lead 52 to be located alongside the LV, and a sonomicrometer crystal 72 is incorporated within a distal segment of the lead body 36 of RV lead 32 An additional sonomicrometer crystal 74 is located more proximally on the RA lead body 15 to locate it in the RA or SVC. The sonomicrometer crystal 74 could alternatively be located more proximally on RV lead body 56 to locate it in the RA or SVC. However, additional lead conductors would be necessary in that case for connection with the sonomicrometer crystal 74. Additionally or alternatively, a sonomicrometer crystal 74' is depicted as incorporated within a more proximal segment of the CS lead body 56 of LV/CS lead 52 to be located alongside the LA at a distance from the sonomicrometer crystal 72.

The sonomicrometer crystals 70, 72, and 74 or 74' can each be formed as a cylindrical piezoelectric crystal tube sandwiched between an inner tubular electrode and an outer tubular electrode and fitted around the lead body 36 of the type described in U.S. Pat. No. 5,795,298. Various sonomicrometer systems for measuring distance between an driven piezoelectric crystal acting as a transmitter of ultrasonic energy and a receiving piezoelectric crystal that vibrates when exposed to the ultrasonic energy and provides an output signal are disclosed in U.S. Pat. Nos. 5,779,638, 5,795,298, 5,817,022 and 5,830,144. Cylindrical receiving crystals are mounted to an ECG mapping lead body and coupled to the lead conductors in the '298 patent, and the receiving crystals are employed with externally located transmitting crystals to provide a way to locate the mapping electrodes in the body without use of fluoroscopy.

In the illustrated embodiment, the LA lead conductors of LV/CS lead 52 that are connected to the more proximal LA CS pace/sense electrodes 28 and 30 are also connected to the inner and outer tubular electrodes of the sonomicrometer crystal 74' respectively Similarly, the LV lead conductors of LV/CS lead 52 that are connected to the more distal LV CS pace/sense electrodes 50 and 48 are also connected to the inner and outer tubular electrodes of the sonomicrometer crystal 70, respectively. The RV lead conductors of RV lead 32 that are connected to the RV pace/sense electrodes 40 and 38 are also connected to the inner and outer tubular electrodes of the sonomicrometer crystal 72, respectively. The RA lead conductors of RA lead 16 that are connected to the RA pace/sense electrodes 24 and 22 are also connected to the inner and outer tubular electrodes of the sonomicrometer crystal 74, respectively.

The outer tubular electrodes of the piezoelectric crystals 70, 72, 74, and 74' can also be employed as an indifferent pace/sense electrode to provide bipolar pacing and sensing replacing the indifferent ring-shaped pace/sense electrodes on the same lead body. The piezoelectric crystals 70, 72, 74, and 74' can be located distal to or between pace/sense electrodes or proximal to the pace/sense electrode or electrodes as shown. The particular depicted locations and relative sizes and spacings between pace/sense electrodes and sonomicrometer crystals are not necessarily to scale and are exaggerated for convenience of illustration.

It will also be understood that the IPG 14 can comprise an ICD IPG, and that the one or more or the leads 16, 32 and 52 can also incorporate cardioversion/defibrillation electrodes and lead conductors extending thereto through the lead bodies for delivering atrial and/or ventricular cardioversion/defibrillation shocks in any of the configurations and operating modes known in the art.

The sonomicrometer crystals 70, 72, 74 and 74' are thereby disposed apart by the RV-LV distance (denoted as D1 in FIG. 1), the LV-RA distance (denoted as D2 in FIG. 1), the RV-RA distance (denoted as D3 in FIG. 1), and the RV-LA distance (denoted as D4 in FIG. 1). The RV-LV distance between the RV and LV crystals is a measure of LV dimension, and changes in the LV dimension over the cardiac cycle are strongly correlated with changes in LV volume as the LV fills during diastole and empties during systole. The LV-RA distance between the LV and RA crystals varies as a function of RA mechanical activity as the RA fills and empties in a pattern during normal sinus rhythm that markedly differs from the pattern exhibited during atrial fibrillation and other forms of ineffective atrial contraction. The RV-RA distance and RV-LA distance between the RV sonomicrometer crystal and the respective RA and LA sonomicrometer crystals varies as a function of a mixture of atrial and ventricular activity. Typically, only one of the RA or LA sonomicrometer crystals 74 or 74', respectively, would be provided to determine RV-RA or RV-LA distances, respectively, and so the following description assumes this to be the case for simplicity of description.

Figure 2:
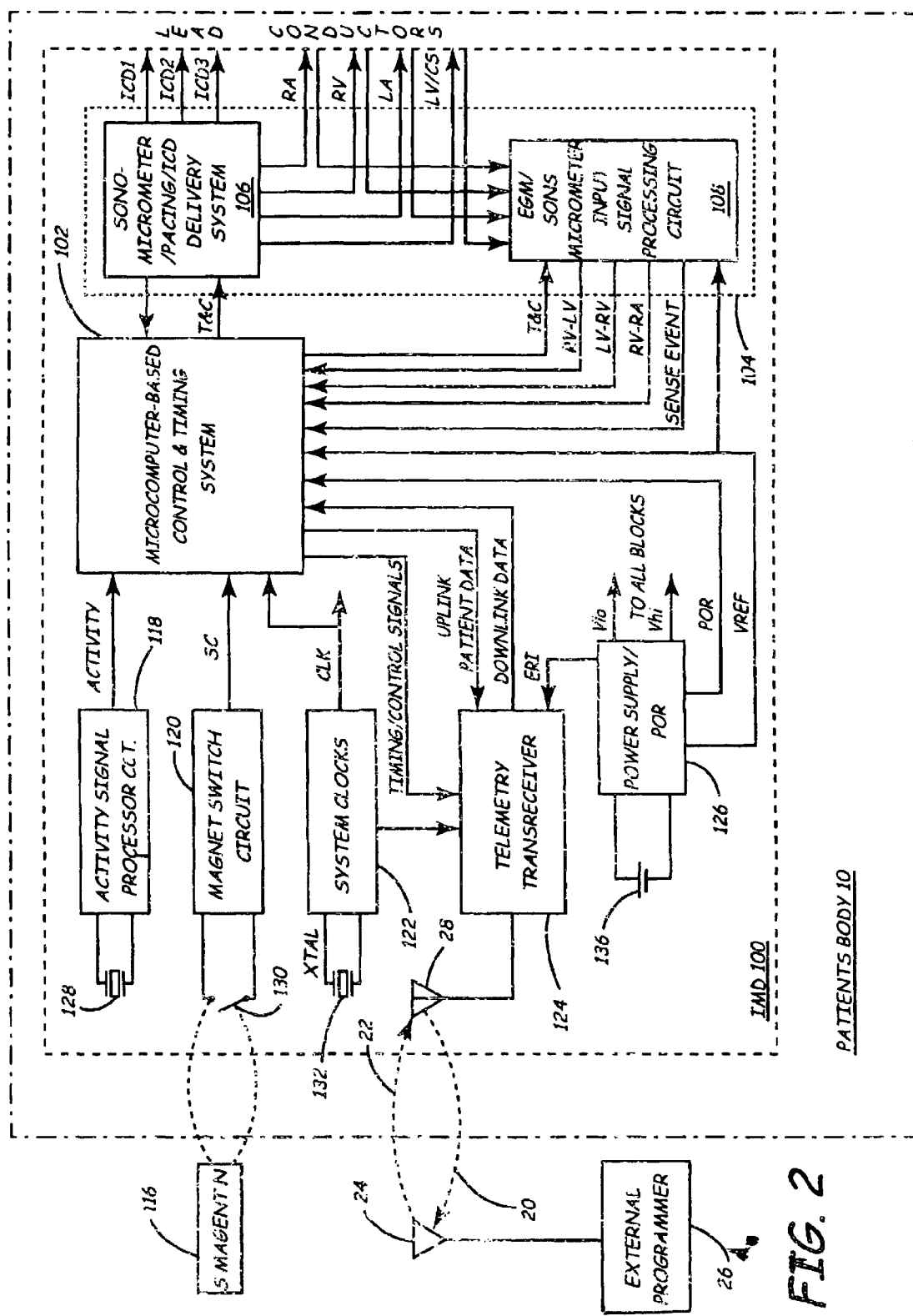
FIG. 2 is a simplified block diagram of one embodiment of IMD circuitry and associated leads employed in the system of FIG. 1 enabling selective therapy delivery and/or derivation of dimension signals across the ventricles and between the ventricles and the atria.

FIG. 2 depicts a system architecture of an exemplary multi-chamber monitor/therapy delivery IMD circuit 100 implanted within a hermetically sealed housing into a patient's body 10 in the manner of IPG 14 described above that provides delivery of a therapy and/or physiologic input signal processing through the RA, LA, RV and LV lead conductor pairs. The IMD circuit 100 optionally includes an ICD function of delivering cardioversion/defibrillation shocks through ICD leads in a manner well known in the art. The components of IMD circuit 100 can be selectively configured to derive the RV-LV, LV-RA, RV-RA, and RV-LA distance signals in order to directly monitor left ventricular function without entering the left side of the heart and to monitor atrial mechanical function in conjunction with the monitoring of the heart, the diagnosis of arrhythmias and heart failure, and the delivery of appropriate therapies. Preferably, the RV-LV, LV-RA AND RV-RA distance signals are derived and employed in the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, monitoring of respiratory rate and the like.

The IMD circuit 100 has a system architecture that is constructed about a microcomputer-based control and timing system 102 that varies in sophistication and complexity depending upon the type and functional features incorporated therein. The functions of microcomputer-based multi-chamber monitor/therapy delivery system control and timing system 102 are controlled by firmware and programmed software algorithms stored in RAM and ROM including PROM and EEPROM and are carried out using a CPU, ALU, etc., of a typical microprocessor core architecture. The microcomputer-based multi-chamber monitor/therapy delivery system control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber IMD circuit 100 can be accomplished with dedicated circuit hardware or state machine logic rather than a programmed microcomputer.

The multi-chamber IMD circuit 100 also typically includes patient interface circuitry 104 for receiving signals from the above-described sensors and pace/sense electrode pairs located at specific sites of the patient's heart chambers to derive heart failure parameters and to time delivery of multi-chamber pacing therapies, particularly AV synchronous, bi-ventricular pacing therapy, to the heart chambers. The patient interface circuitry 104 therefore comprises a sonomicrometer/therapy delivery system 106 and a physiologic input signal processing circuit 108 that are both coupled with the above-described RA. RV, LA and LV lead conductor pairs and described in further detail in reference to FIG. 3. The patient interface circuitry 104 can be configured to include circuitry for delivering cardioversion/defibrillation shocks and/or cardiac pacing pulses delivered to the heart or cardiomyostimulation to a skeletal muscle wrapped about the heart. A drug pump for delivering drugs into the heart to alleviate heart failure or to operate an implantable heart assist device or pump implanted in patients awaiting a heart transplant operation can also be incorporated into the sonomicrometer/therapy delivery system 106. The therapy delivery capabilities of sonomicrometer/therapy delivery system 106 can be eliminated or disabled if IMD circuit 100 is configured as a cardiac monitor.

A battery provides a source of electrical energy to power the multi-chamber IMD circuit 100 and to power any electromechanical devices, e.g., valves, pumps, etc. of a substance delivery multi-chamber monitor/therapy delivery system, or to provide electrical stimulation energy of an ICD shock generator, cardiac pacing pulse generator, or other electrical stimulation generator associated therewith. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 2.

Virtually all current monitor/therapy delivery system circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

RAM memory registers in microcomputer-based control and timing system 102 may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber IMD circuit 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber IMD circuit 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

Uplink and downlink telemetry capabilities are provided in the multi-chamber IMD circuit 100 to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the multi-chamber IMD circuit 100 to the external programmer or other remote medical device 26 in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

Figure 3:
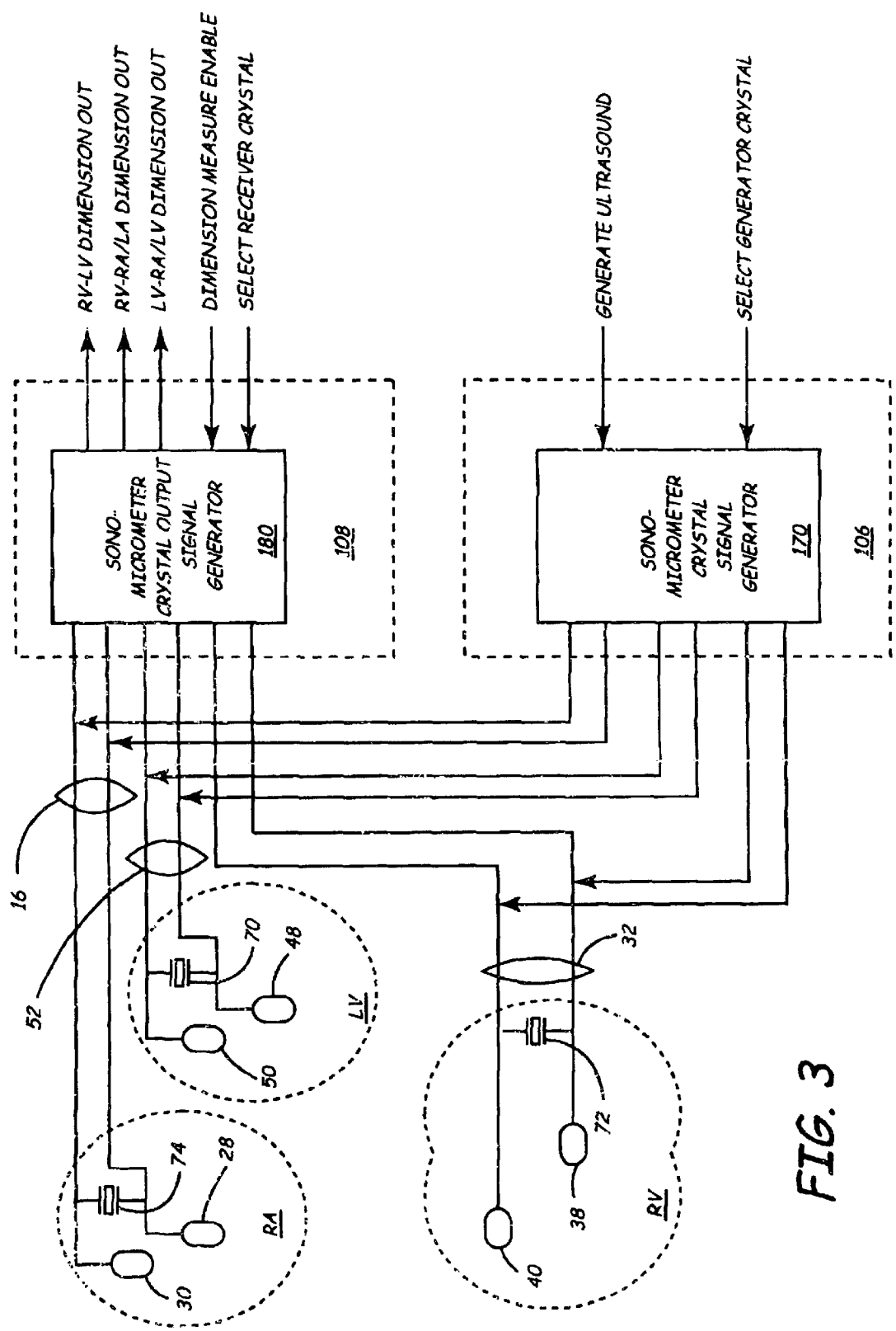
FIG. 3 is a simplified block diagram of a multi-chamber measurement system for selectively deriving dimension measurements between selected pairs of sonomicrometer piezoelectric crystals arranged about the heart.

The physiologic input signal processing circuit 108 in multi-chamber monitor/therapy delivery systems as IMD circuit 100 includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal-processing stages for detecting the occurrence of a P-wave or R-wave, respectively and providing an RA-SENSE. RV-SENSE, LA-SENSE and/or LV-SENSE event signal to the control and timing system 102. Such an RV sense amplifier circuit i48 is depicted in FIG. 3, for example. Timing and control system 102 responds in accordance with its particular operating system to deliver or modify a pacing therapy, if appropriate, or to accumulate data for uplink telemetry transmission or to provide a Marker Channel® signal in a variety of ways known in the art.

With IMD circuit 100 configured as an AV sequential, bi-ventricular pacing system, the sonomicrometer/therapy delivery system 106 preferably comprises an RA pacing output pulse generator, an RV pacing pulse generator, an LV pacing pulse generator and optionally an LA pacing pulse generator selectively coupled in each case to an RA, RV, LV and LA pace electrode pair which can be programmably selected as described above. For example, the RA pacing output pulse generator can be coupled to the RA lead conductors, the RV pacing pulse generator can be coupled to the RV lead conductors, the LV pacing pulse generator can be coupled to the LV lead conductors, and the LA pacing pulse generator can be coupled to the LA lead conductor pair for bipolar pacing in relation to each chamber. Two, three or four chamber synchronized pacing is effected employing combinations of these pacing pulse generators and following a pacing timing algorithm carried out by microcomputer-based timing and control system 102 in a manner disclosed in commonly assigned, U.S. Pat. No. 5,902,324. The present invention seeks to optimize the timing of delivery of RV and LV pacing pulses to alleviate symptoms of heart failure and optimize cardiac output as a function of measured changes in at least the dimension D2 of FIG. 1.

FIG. 3 schematically depicts certain of the components of sonomicrometer/therapy delivery system 106 and input signal processing circuit 108 in relation to the pace/sense electrodes and the sonomicrometer crystals 70, 72 and 74 or 74' of the RA, LV/CS and RV leads. Not all of the components of the sonomicrometer/therapy delivery system 106 (particularly the pacing pulse generators) and input signal processing circuit 108 (particularly the sense amplifier circuits) are depicted in FIG. 3 in order to make its depiction of the components of interest clearer.

To this end, FIG. 3 shows that the sonomicrometer/therapy delivery system 106 comprises a crystal signal generator 170 for supplying an oscillating drive signal to a programmably selected one of the sonomicrometer crystals 70, 72 and 74 (the driven or ultrasound transmitter crystal). A low energy drive signal at about 1.0 MHz can be applied by crystal generator 170 to the selected one of the sonomicrometer crystals 70, 72 and 74 to transmit the ultrasonic signal through the heart tissue and to induce oscillations at the same frequency in the other selected one or more of the sonomicrometer crystals 70, 72 and 74. For example, when the driven crystal is sonomicrometer crystal 72 coupled through the RV lead conductor pair with the crystal signal generator 170, the transmitted ultrasonic wave energy causes the other sonomicrometer crystals 70 and 74 to act as receiver sonomicrometer crystals. Sonomicrometer crystals 70 and 74 vibrate at their resonant frequencies and generate receiver signals in the manner of a microphone after an RV-LV and RV-RA time delay dependent upon the instantaneous distances denoted D1 and D3 of FIG. 1, respectively, and the speed that the ultrasound frequency signals travel through blood and heart tissue. The received signals are conducted through the LV and LA lead conductors to and detected by a sonomicrometer signal processor circuit 180 within the input signal processing circuit 108. The RV-LV and RV-LA time delays depend upon the fixed speed of sound through blood heart tissue, which typically is a constant 1540 meters/second, and the instantaneous distance between the ultrasound transmitter crystal and ultrasound receiver crystal. That distance or dimension varies as a function of how much the LV and RA contracts in the systolic phase and relaxes in the diastolic phase. Sets of instantaneous dimensions D1 and D3 can be determined during programmed sample windows of the paced or intrinsic heart cycle from the measured RV-LV and RV-RA time delays collected as the driven sonomicrometer crystal is periodically energized at a defined sample frequency during the defined sample window.

Alternatively, the dimensions D1, D2 and D3 can be derived by cycling through a routine of selecting and applying ultrasound energy to RV sonomicrometer crystal 72 and measuring the dimensions D1 and D2 as described above and then applying ultrasound energy to LV sonomicrometer crystal 70 or LA sonomicrometer crystal 74 and measuring dimension D3 from the signal received at the other of the LV sonomicrometer crystal 70 or LA sonomicrometer crystal 74. A similar routine may be established if the LA sonomicrometer crystal 74' is located in relation to the LA as depicted in FIG. 1.

This determination of the dimensions D1, D2, and D3 compiles accurate data of the excursions of the LV and RA walls due to the locations of the sonomicrometer crystals 70 and 74 without requiring perforation of or intrusion of a sensor into the LV chamber and formation of harmful thromboembolisms.

The RV, LV and LA lead conductors can be employed to power the driven sonomicrometer crystal and to detect the induced ultrasonic frequency signals on the designated receiver sonomicrometer crystals without compromising the delivery of pacing pulses or the sensing of the atrial and ventricular EGM. The sonomicrometer crystals 70, 72, and 74 exhibit high impedance except at their resonance frequency of about 1.0 MHz which is orders of magnitude above pacing pulse and EGM frequency bandwidths. Therefore, the sonomicrometer crystals 70, 72, and 74 act as open circuits and do not conduct or draw current during normal pacing operations but can be periodically energized during sample windows to gather data for storage or for controlling IMD operating parameter values and modes as described further below. The high frequency ultrasound energy is blocked by a filter at the sense amplifier input and protection circuitry at the output of the pacing pulse generators.

Experimental Results:

An animal study was undertaken to assess the feasibility using the sonomicrometer system and method in a mammalian heart under a number of conditions. The study involved the attachment of sonomicrometry crystals near the tips of standard pacemaker leads, to conduct real-time measurements of intracardiac dimensions. The leads were positioned acutely in the CS, the RA appendage, and the RV apex. The path or vector between the LV crystal on the CS lead and RV crystal on the RV lead passed obliquely through the LV. The RV-LV (D1) distance measurement was hypothesized to provide an index of LV mechanical activity. Similarly, the LV-RA (D3) distance measurement was hypothesized to provide an index of atrial mechanical activity, and the RV-RA (D2) distance measurement was hypothesized to provide a combination of RV and RA mechanical activity. Prototype equipment was developed and five canines were studied acutely to demonstrate proof-of-concept of intracardiac distance measurements and to provide anecdotal evidence of the information content of these distance measurements.

The sonomicrometer measurements of distance and motion were accurate when compared with caliper and fluoroscopic distance measurements. The distance between the LV and RV crystals consistently decreased during-shaped LV ejection. LV stroke volume was estimated from the systolic shortening of the LV-RV distance with a standard deviation of 1.0 to 1.5 ml in 4 canines. However, this estimator of stroke volume was sensitive to changes in crystal location and/or LV dynamics. The systolic rate of shortening of the LV-RV distance was highly correlated with the maximum dP/dt of the LV (which is generally accepted as an index of cardiac contractility). Decreases in the LV-RA distance occurred during atrial contraction, and often designated the opening of the mitral/tricuspid valves. Finally, the morphology of the RV-RA distance signal was relatively inconsistent between canines. The encouraging results of this study warrant further investigation into specific applications of lead-based sonomicrometry.

Custom annular piezoelectric crystals (Sonometrics Corp., London, Ontario, Canada) were fitted around the outer insulation of a Model 2987 coronary sinus lead, a Model 4024 RV lead, and a Model 4524 RA lead. The crystals were located about 1 cm proximal to the lead tips. The crystal dimensions were approximately 0.095 inches inner diameter, 0.010 inches wall thickness, and 0.106 inches in length. The twisted pair of conductors for each crystal was passed outside of the lead insulation and was attached periodically to the lead body with shrink-wrap tubing. The associated electronics for distance measurement were obtained as an off-the-shelf system from Sonometrics, Inc. Electric pulses ("pings") were delivered to a given crystal for transmission, and the time to reception by the other crystals was recorded with a 16 ns resolution (equivalent to 24 micrometer distance resolution). The pings consisted of a single-phase square wave of 28 volts amplitude and about 900 ns duration. The resonance frequency of the crystals was about 550 kHz. The cylindrical structure of the crystals resulted in a nearly omnidirectional emission pattern; alignment of the crystals was not necessary.

A total of five canines were anesthetized with thiopental and/or isoflurane. Surgical preparation included a right thoracotomy in the $4^{th}$ or $5^{th}$ intercostal space, a jugular venous cut down for passage of pacing leads, and a carotid or femoral arterial cut down for placement of a Millar Catheter. An ultrasonic flow probe (20A probe from Transonic Systems Inc., Ithaca N.Y.) was placed around the proximal aorta for measurement of LV ejection. A 5 F Millar Catheter (Millar Instruments Inc, Houston, Tex.) was positioned in the left ventricle. The RV lead was positioned in the apex and the RA lead was positioned in the appendage according to common practice. Multiple locations of the CS were investigated with the goal of obtaining a path between the LV and RV crystals that traversed the LV. In two canines (dog 3 and dog 4), a coronary venogram was performed to guide placement of the LV crystal near the center of the basal end of the LV free wall. Dog 3 and dog 4 also had a preliminary echocardiogram to rule out regurgitation of the mitral valve. The AV node was ablated in dog 2 and dog 5. The CS lead and aortic flow probe could not be successfully positioned in one canine (dog 5).

During the studies, the distance between each crystal and the other two was measured at a sampling frequency of 200 Hz. The sampling times of aortic flow, LV pressure, and surface ECG were equivalent to that of the sonomicrometer. Recordings were conducted during baseline conditions and under a variety of interventions, including: variable rate AOO pacing, VOO pacing, DOO pacing, dobutamine infusion, arterial hemorrhage, epinepherine injection, helium desaturation, apnea, bilateral carotid occlusion, inferior vena cava occlusion, coronary artery occlusion, and induction of atrial and ventricular arrhythmias. The raw sonomicrometer signals were first processed to remove outliers. The outliers occurred when either 1) electrical cross-talk between the sending and receiving crystals produced a nearly instant "reception" at the receiving crystal, and therefore a near zero distance measurement, or 2) the sound transmission never triggered the receiving system, therefore producing a maximum distance measurement. The outliers occurred rarely and were replaced by linear interpolation between neighboring non-outlier points.

The LV and RA sonomicrometer crystals were attached to the tips of a standard micrometer (distance resolution $20 \mu m$) to validate the sonomicrometer measurements of distance. The crystals were then lowered into a tank of tap water and the sonomicrometer distance was compared to the micrometer distance.

Fluoroscopic recordings were obtained in multiple planes to validate the sonomicrometer measurements of cardiac motion. A search was conducted for a fluoroscopic imaging plane where the distance between the LV and RV crystals was maximized. The fluoroscopy equipment was then positioned to allow free rotation of the arm in the plane that bisected the line connecting the LV and RV crystals (i.e., maintaining the maximum distance between the LV and RV crystals during the rotation). The arm was rotated until the motion of the two crystals was approximately constrained to lie along the line containing the two crystals. The imaging plane was then rotated 90° to display the plane that showed the best 2-D approximation of the crystal motion. Using calipers on a video monitor, the distances between crystals was measured frame-by-frame throughout the cardiac cycle. These measurements were conducted on dog 1, dog 3 and dog 4.

A Bland-Altman plot comparing the micrometer and sonomicrometer measurements was prepared. Because the micrometer measured the distance between the centers of the crystals, whereas in theory the sonomicrometer measured distances between the edges of the crystals, the micrometer measurements were consistently larger by about 1 mm. The difference between the two measurements tended to decrease with increasing distances, perhaps because the precise velocity of sound was slightly different than the nominal value for water (1480 m/s). Given the simplicity of this comparison technique, there is strong agreement between the two methods.

The cyclic variation of the LV-RV distance in dog 1 was 7.4% from fluoroscopy and 6% from the sonomicrometer. For dog 3, the cyclic variation of the LV-RV distance was 4.4% from fluoro and 4.4% from the sonomicrometer. For dog 4, the cyclic variation of the LV-RV distance was 6.4% from fluoro and 8.7% from the sonomicrometer.

Although the cyclic variations in the RV-LV distance as measured by the sonomicrometer are significantly smaller than would be expected for a measurement across the LV, the sonomicrographic measurements are substantiated by the fluoroscopic measurements. One possible explanation for the small variations in RV-LV distance during the cardiac cycle is the fact that the myocardium thickens as the LV ejects, and the RV-LV distance vector traverses the septum and the LV free wall as well as the LV lumen.

Figure 4:
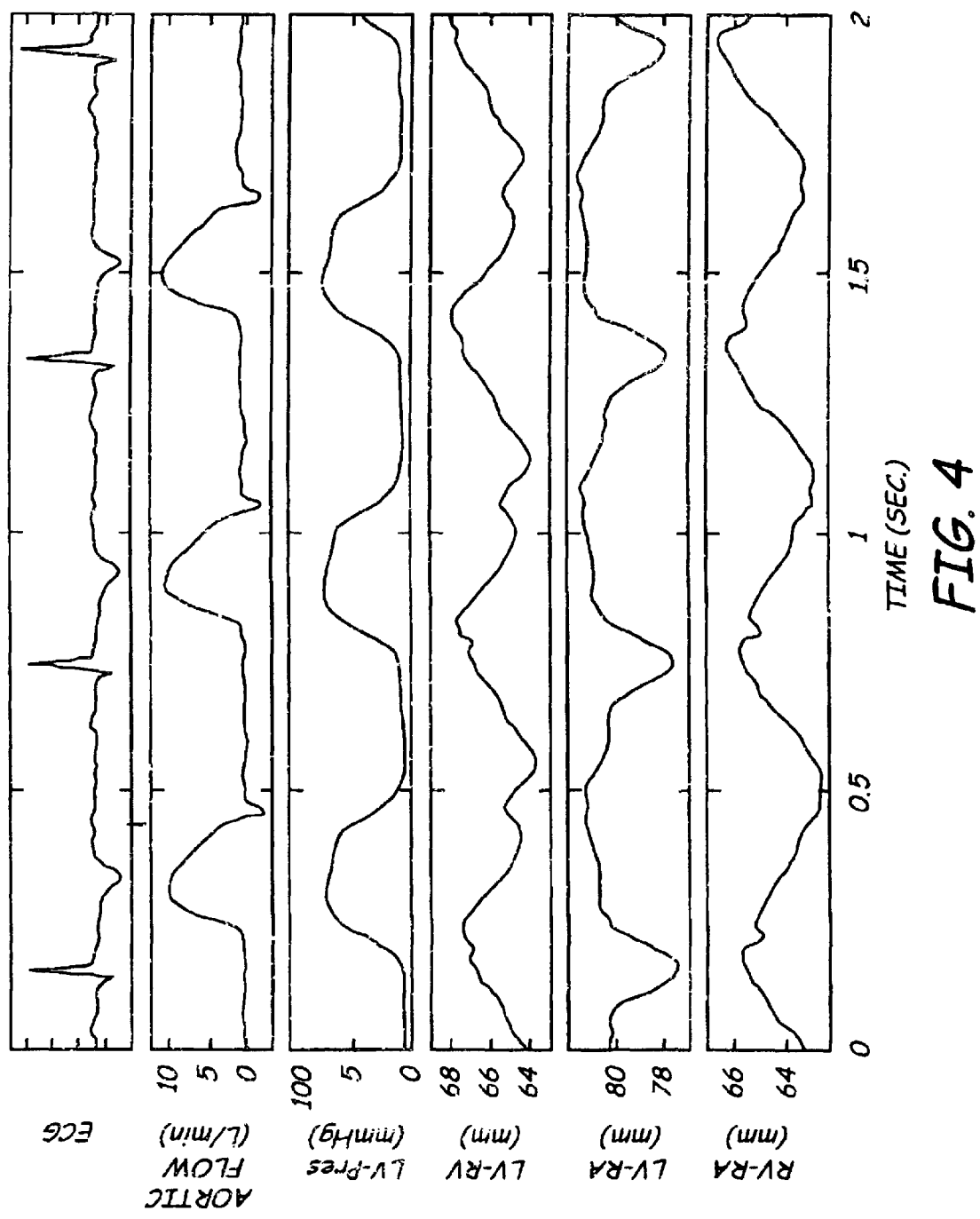
FIG. 4 illustrates signal tracings of ECG, aortic flow, LV blood pressure and RV-LV, LV-RA and RV-RA distance signals obtained in a dog study.

An example recording of the ECG, aortic flow, LV pressure, and the three sonomicrometer signals during intrinsic rhythm is shown in FIG. 4. The systolic decrease in the RV-LV distance coincides with the ejection of blood from the LV. The LV-RA distance decreases slightly when the mitral/tricuspid valves open (after LV pressure rapidly drops), and decreases rapidly after each P wave of the ECG. Finally, the RV-RA distance generally increases during filling of the heart and decreases during emptying of the heart. Also, the RV-RA signal contains a notch during the isovolumic contraction period.

Figure 5:
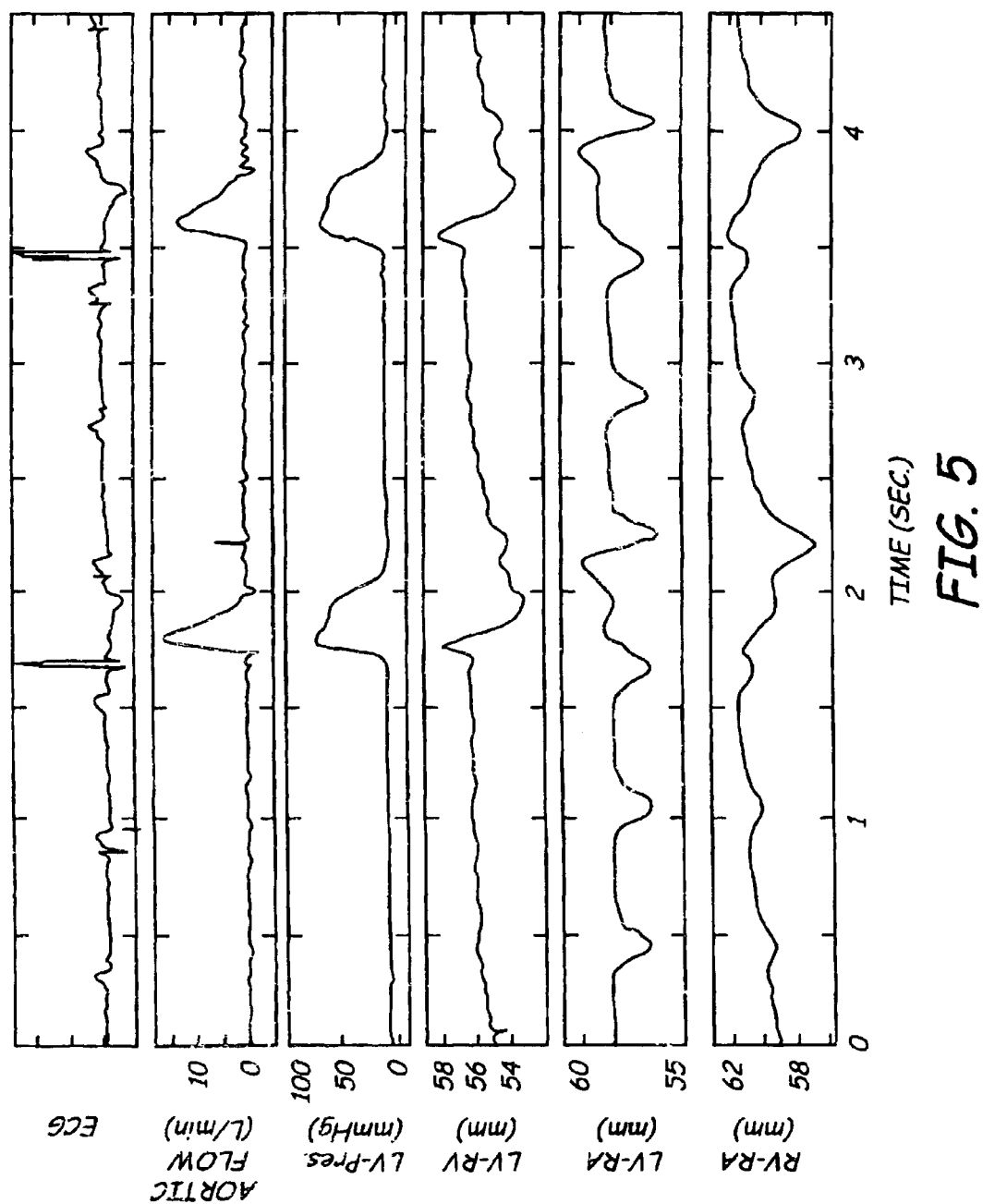
FIG. 5 illustrates tracings of the signals of FIG. 4 during dual chamber (DOO) pacing of the RA and RV with intermittent ventricular capture in a dog having the AV node ablated.

FIG. 5 contains a sample recording during DOO pacing with intermittent ventricular capture in a dog with complete heart block. The separation of atrial and ventricular contractions in this example serves to simplify interpretation of the sonomicrometer signals. The RV-LV signal continuously increases during ventricular asystole and rapidly decreases during ventricular systole. The LV-RA signal decreases after each P wave on the ECG. In contrast to FIG. 4, the LV-RA signal does not begin a slow descent before the P-wave, because the atria are not able to empty into the filled ventricles. The RV-RA signal in this example appears as a combination of the LV-RA and RV-LV signals.

Figure 6:
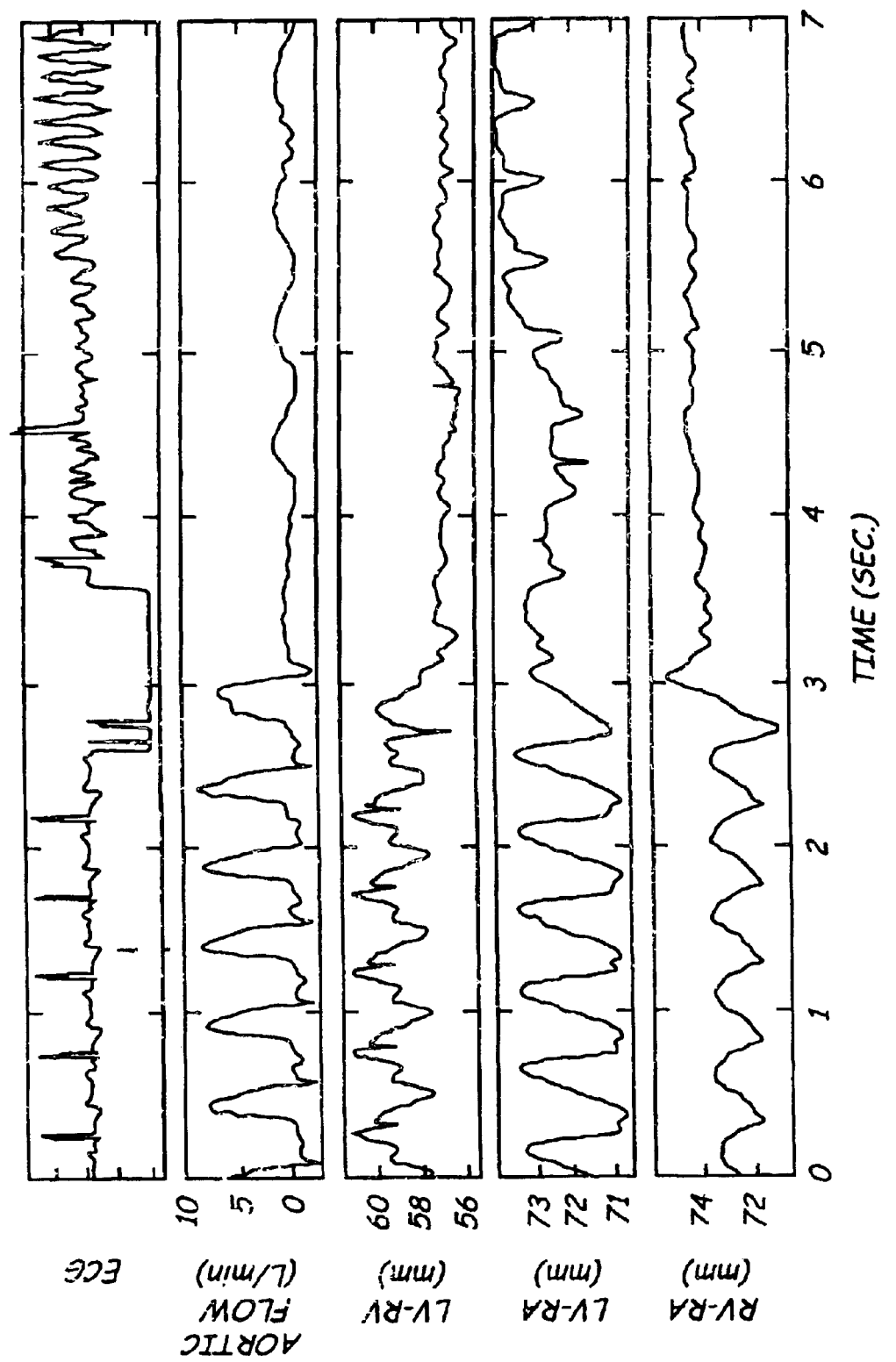
FIG. 6 illustrates tracings of the signals of FIG. 4 before and after induction of ventricular fibrillation (VF) in a dog heart showing determination of atrial contractions during VF by the LV-RA distance signal.

FIG. 6 is sample recording during induction of VF via connection of a 9 volt battery to the RV pacing lead for 1 second. The aortic flow instantly ceases, and the LV-RA and RV-RA signals clearly show the cessation of pumping. The LV-RA signal shows uninterrupted atrial contractions after the induction of VF. A more extensive description of the information content of each of the sonomicrometer signals is presented in the sections that follow.

Figure 7:
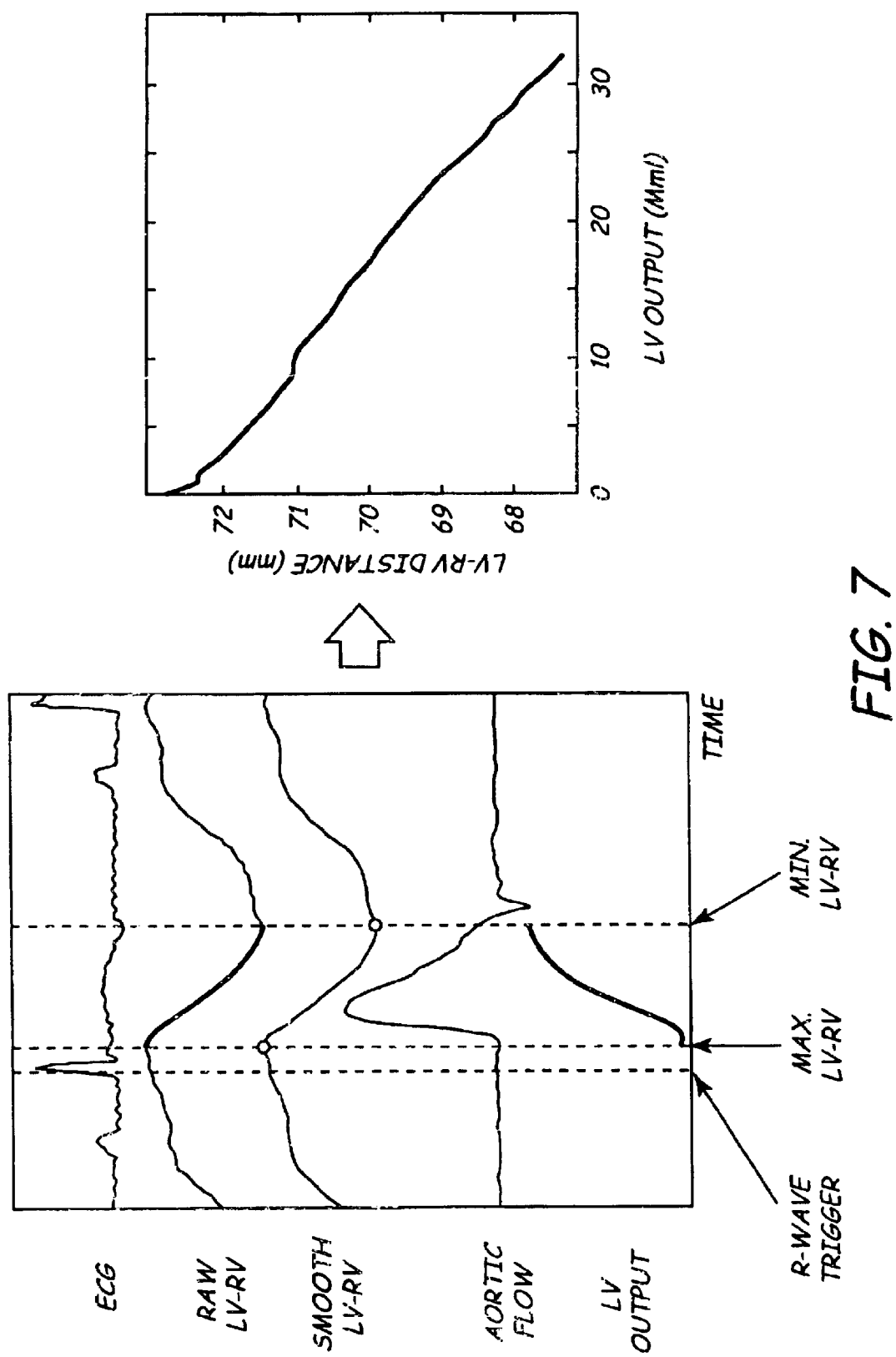
FIG. 7 illustrates the processing of aortic flow and LV-RV distance signals to provide an indication of LV output.

As described above, the RV-LV distance signal shows a characteristic decrease that coincides with LV ejection. This finding prompted an investigation of the relationship between the systolic shortening of the RV-LV distance and the volume ejected from the LV. FIG. 7 shows the algorithm that was used to study this relationship. Following a detected R-wave, the first occurrence of a local maximum in the RV-LV distance signal was taken to be the onset of systolic ejection. The local minimum following this time was taken to be the end of systolic ejection. The aortic flow signal was integrated between these two times to quantify the volume ejected from the LV. Thus, the systolic distance between the CS and RV signals could be compared to the volume ejected from the LV.

Figure 8:
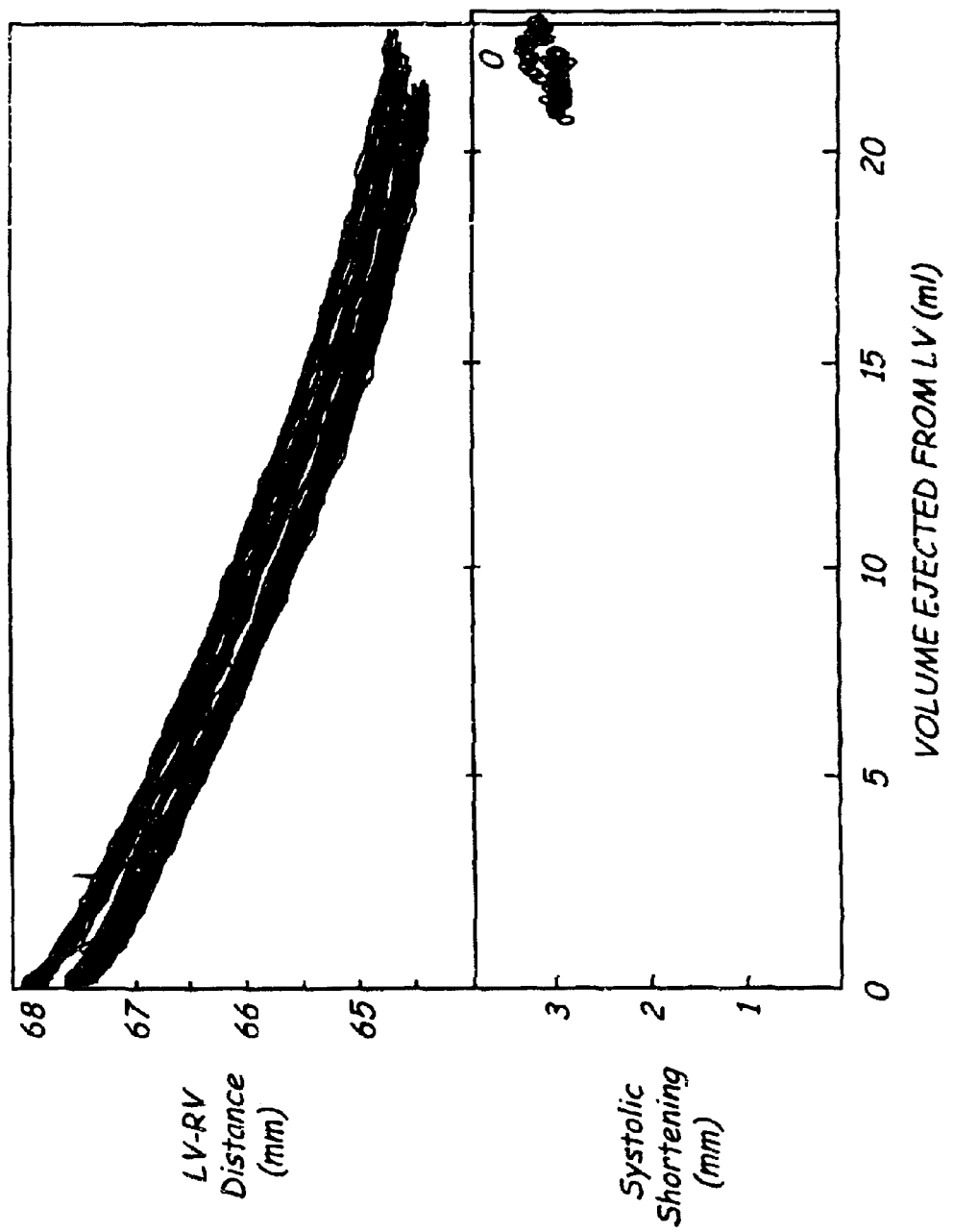
FIG. 8 illustrates signal tracings of a series of LV-RV distance signals versus the change in LV volume during intrinsic heart rhythm in a dog, wherein each line in the upper panel represents one systole and each point in the lower panel represents the systolic shortening versus LV stroke volume.

FIG. 8 shows the relationship between the volume ejected from the LV and the RV-LV distance during normal sinus rhythm. This result is plotted in two ways: as one line for each systole (RV-LV distance vs. volume ejected from the LV), and as one point for each systole (systolic shortening of the RV-LV distance vs. stroke volume). FIG. 8 shows the consistency and near-linearity of the distance to volume relationship.

Figure 9:
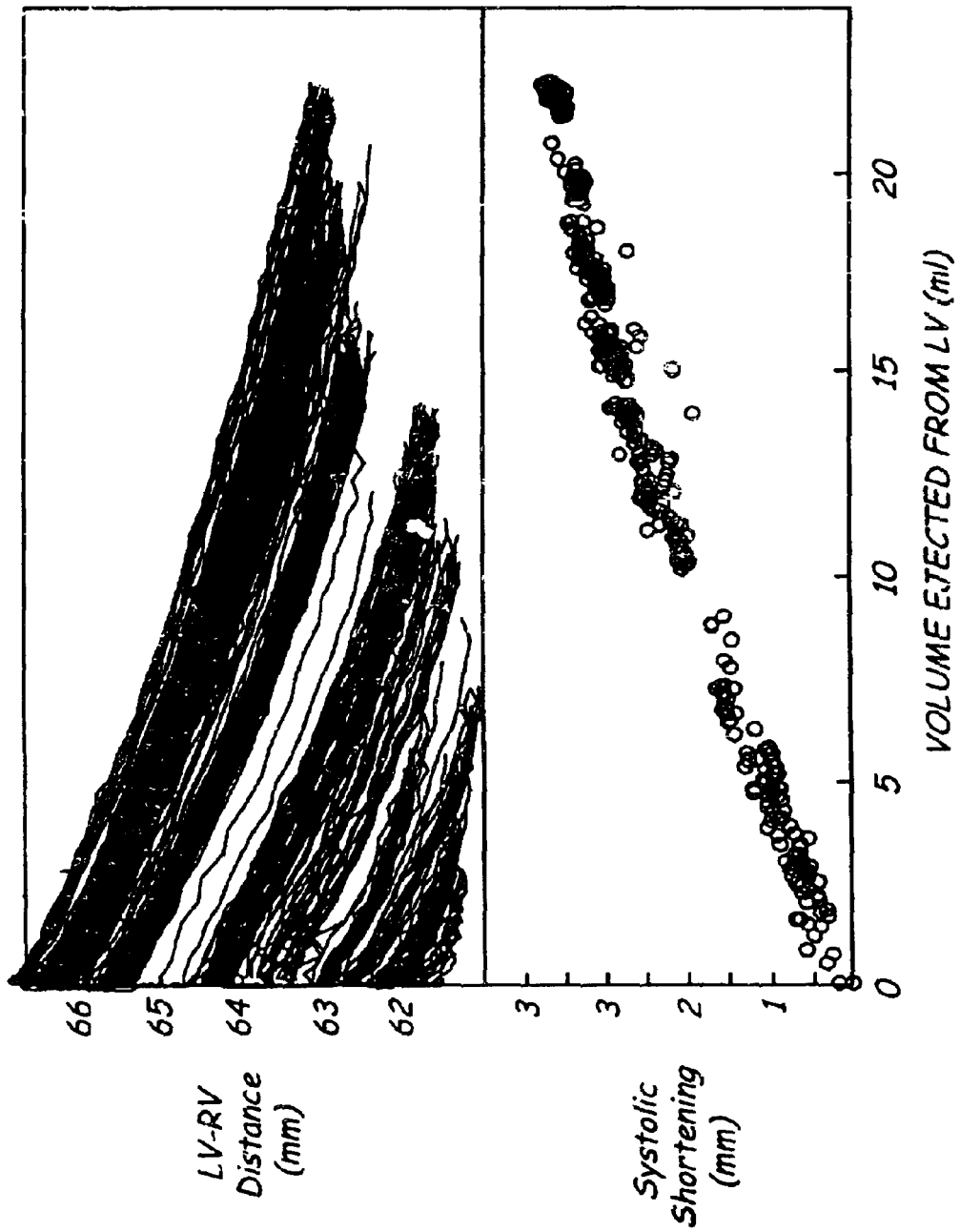
FIG. 9 illustrates signal tracings of a series of LV-RV distance signals versus the change in LV volume during atrial (AOO) pacing of a dog heart over a range of pacing rates, wherein each line in the upper panel represents one systole and each point in the lower panel represents the systolic shortening versus LV stroke volume.

FIG. 9 shows the consistency of the distance to volume relationship when increases in the AOO pacing rate result in decreases in the stroke volume. Not only is the relationship between distance and volume nearly linear, but the relationship is very consistent over a broad range of stroke volumes. FIG. 9 also shows a nearly linear relationship between the systolic shortening and the stroke volume over a large range of stroke volumes. Therefore, a simple model can used to estimate LV stroke volume from the measured systolic shortening.

Figure 10:
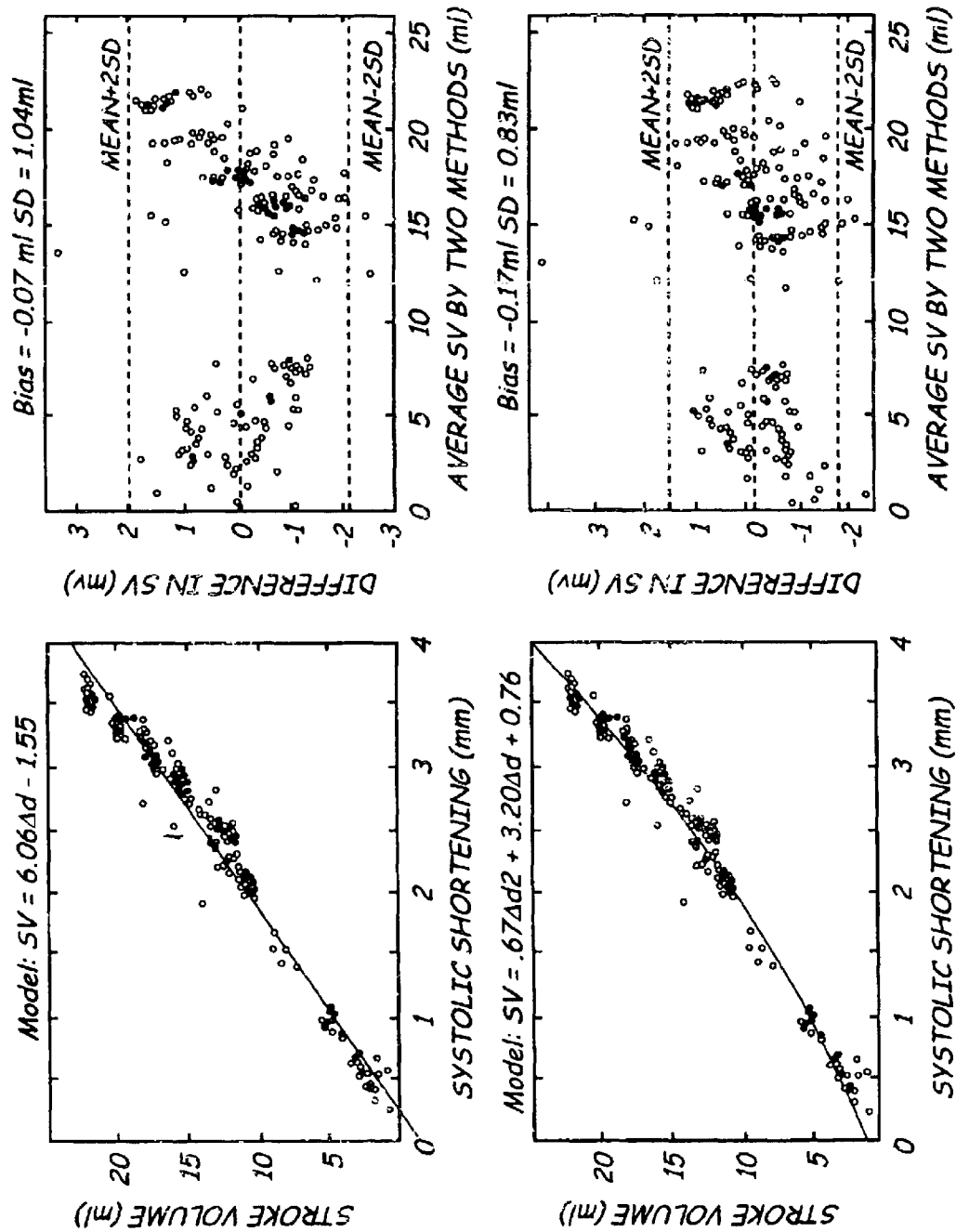
FIG. 10 illustrates linear and quadratic model-based estimators of stroke volume from the measured systolic shortening in a dug study.

FIG. 10 shows the construction and evaluation of model-based estimators of stroke volume from systolic shortening in one of the dogs. A segment of data with a slowly increasing AOO, VOO, or DDD pacing rate was acquired. Every other cardiac cycle of this data was used to construct a least-square-error linear or quadratic model of stroke volume from systolic shortening (left half of FIG. 10). The remaining cardiac cycles were used to evaluate the performance of the model-based estimator, which is reported as the bias and standard deviation from the Bland-Altman plots (right half of FIG. 10). Similar estimators were constructed for four dogs in the study. The standard deviations were in the range of 0.8 to 1.5 ml, and the biases were all less than 0.2 ml. The linear and quadratic models produced similar performance and the performance was very consistent across dogs. Therefore, under the conditions of this study, proper calibration of the RV-LV sonomicrometer signal would result in an estimator of stroke volume with a standard deviation of about 1 ml (or a coefficient of variation of 3 to 5% for nominal cardiac cycles).

Figure 11:
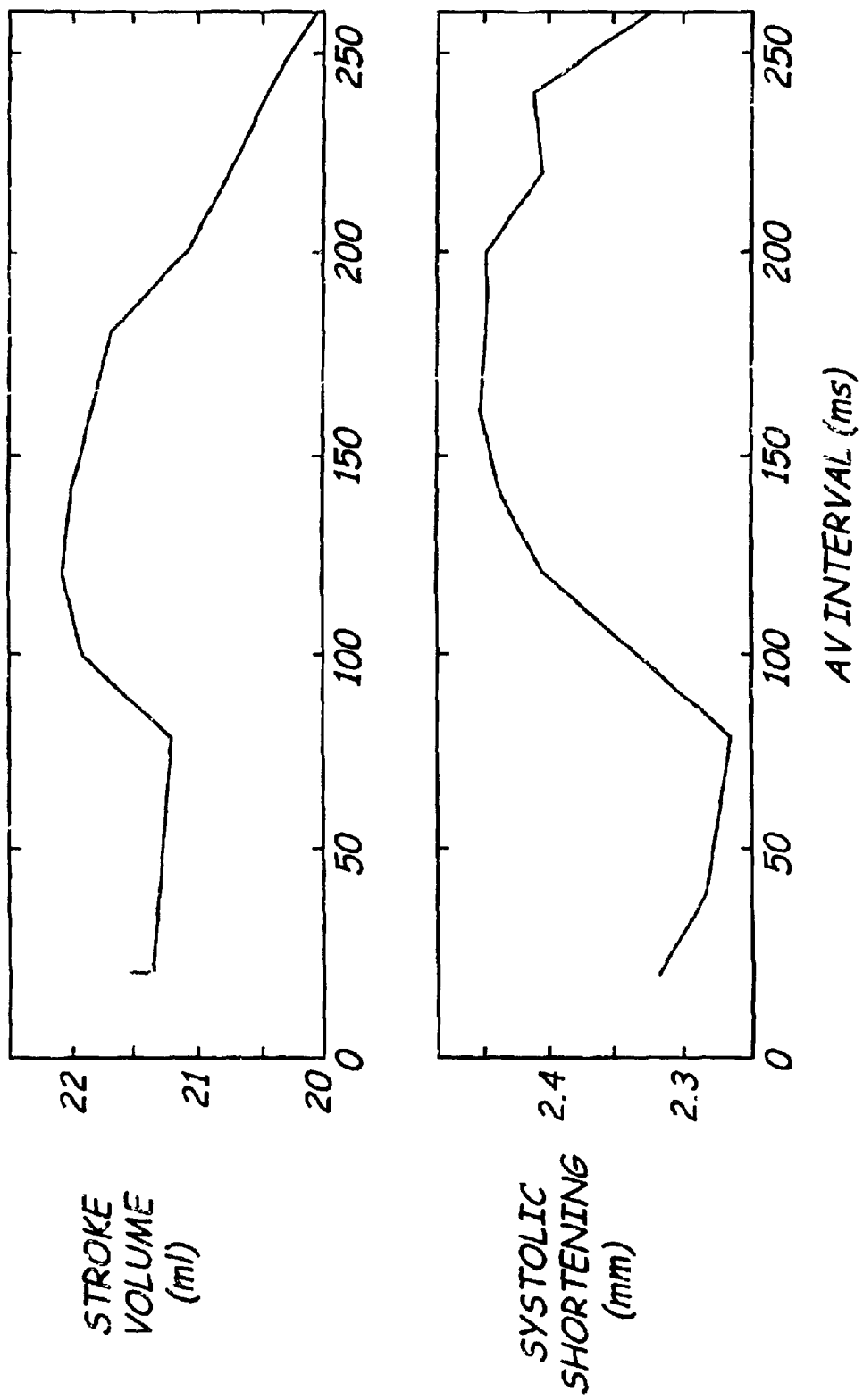
FIG. 11 illustrates stroke volume and systolic shortening of the LV-RA distance as AV interval is changed during dual chamber (DOO) pacing of a dog heart having complete heart block.

FIG. 11 shows similar variations in stroke volume and systolic shortening when AV interval varies from 20–260 ms at a constant DOO pacing rate. Each point on these graphs is the average over 20 cardiac cycles. Although stroke volume shows little variation versus AV interval in a normal, anesthetised dog, the systolic shortening shows promise for tracking even these small variations. From the above analysis, the standard deviation of model-based estimates of stroke volume from the systolic shortening is in the range of 1.0 ml to 1.5 ml. Therefore, an estimate of stroke volume from systolic shortening that is averaged over 20 cardiac cycles has a standard deviation of 0.22 ml to 0.33 ml.

Figure 12:
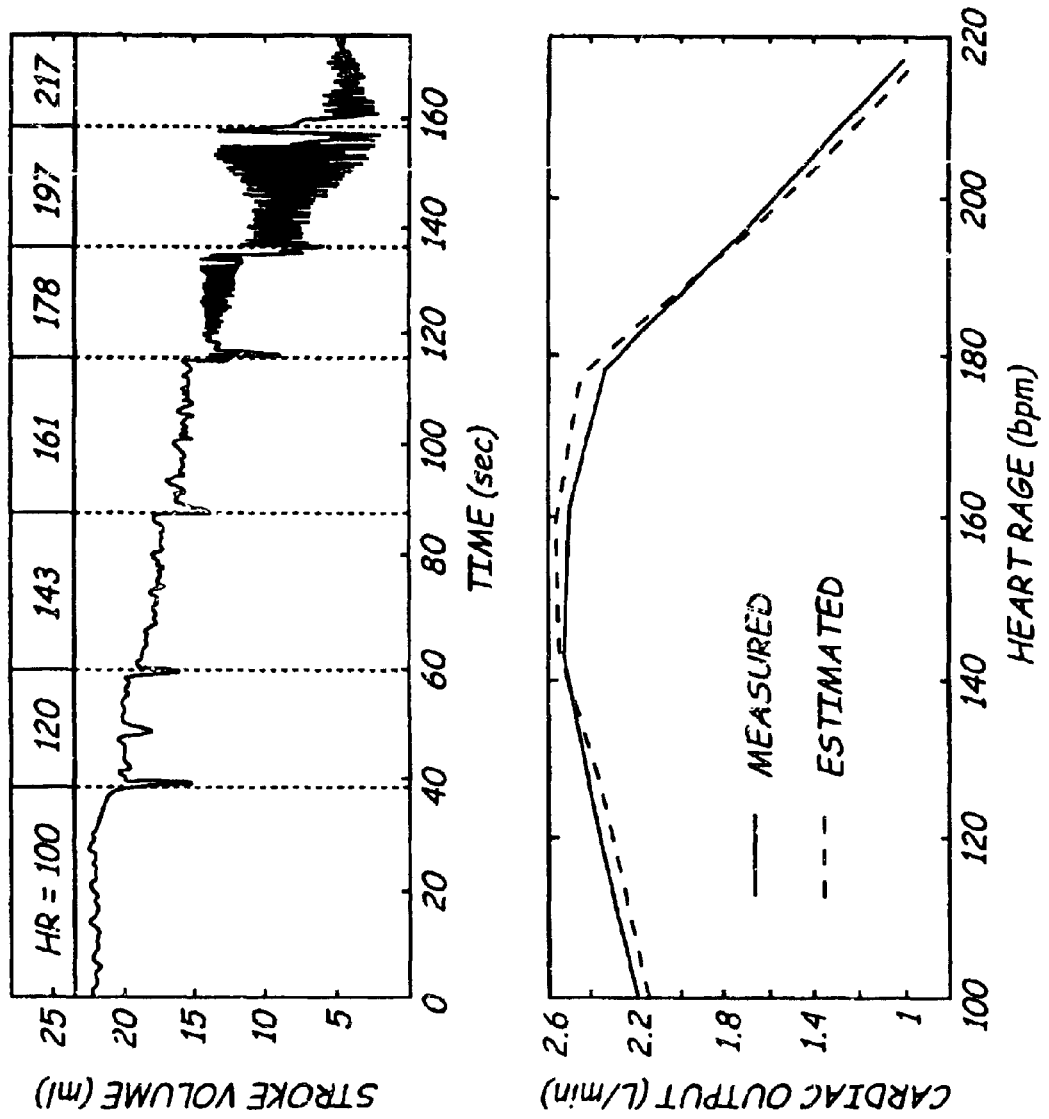
FIG. 12 illustrates the changes in stroke volume and cardiac output with the changes in atrial (AOO) pacing of a dog heart, wherein the cardiac output is estimated from the systolic shortening and the linear model.

The RV-LV distance could also be used to determine when the heart rate is fast enough to cause a decrease in cardiac output. The top panel of FIG. 12 shows the decrease in stroke volume when heart rate increases in a resting animal. The bottom panel shows the corresponding changes in cardiac output when heart rate is increased. The cardiac output is measured directly, and is estimated from the measured systolic shortening and the linear model for this dog. Both the direct and sonomicrometer measurements show decrease in cardiac output when heart rate exceeds 160 BPM.

Although FIGS. 10–12 provide strong evidence that LV stroke volume can be estimated from the RV-LV systolic shortening, there are many circumstances that can change the relationship between the single distance measurement and the left ventricular volume. For example, the development of wall motion abnormalities, mitral regurgitation, ventricular aneurysm, or ventricular remodeling would all be expected to modify the relationship between RV-LV distance and LV stroke volume. Less dramatic changes in LV dynamics, such as those induced by intrinsic vs. paced ventricular excitation, postural changes, and adrenergic responses may also change the relationship between distance and volume.

Figure 13:
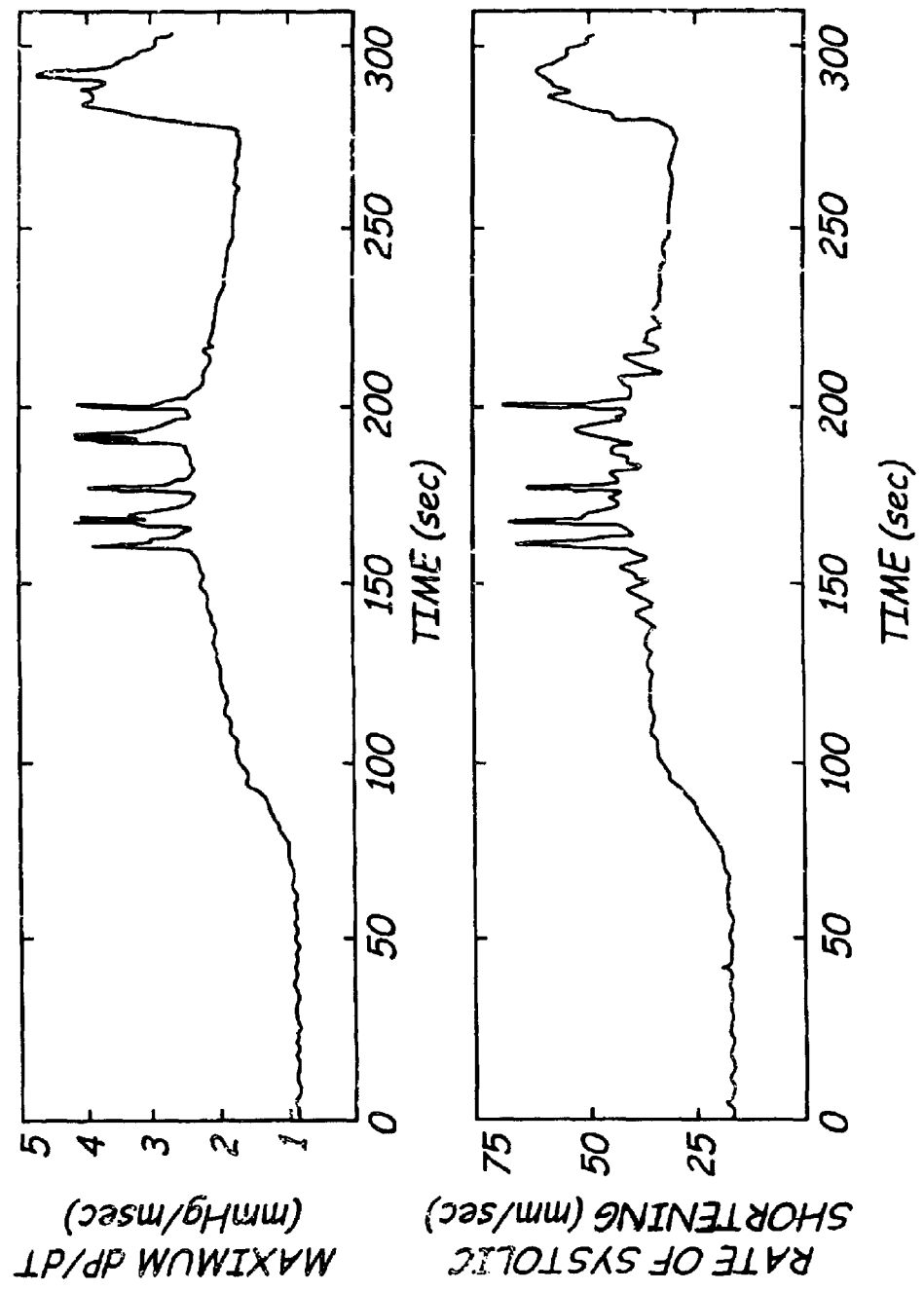
FIG. 13 illustrates the rate of systolic shortening as surrogate metric of cardiac contractility during dopamine infusion into the femoral vein of a dog over 180 seconds with line flushing at 240 seconds.

Three estimates of cardiac contractility were derived from the RV-LV distance signal comprising the duration of ejection, the delay from the R-wave to the beginning of ejection, and the rate of systolic shortening. Of these, the rate of systolic shortening had the strongest correlation with the maximum dP/dt of the LV. FIG. 13 compares the maximum dP/dt to the rate of systolic shortening during dobutamine infusion. The infusion begins at time zero, but only begins to take effect about 70 seconds later. At about 180 seconds, the infusion is stopped, and the infusion tubing is flushed at about 270 seconds. Numerous PVC's occurred in the range of 160 to 190 seconds. The rate of the systolic shortening is highly correlated with the maximum dP/dt in this case.

Figure 14:
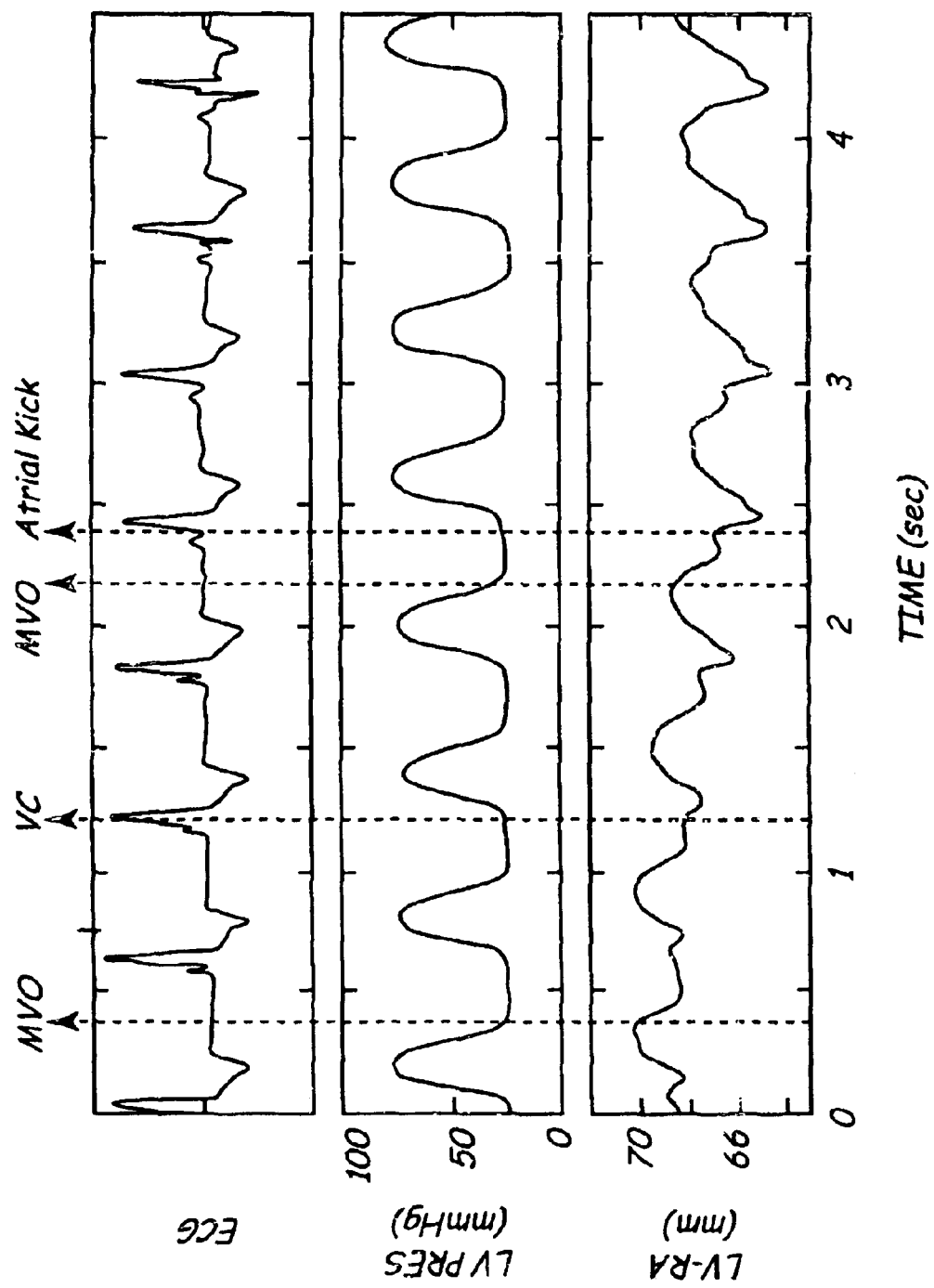
FIG. 14 illustrates signal tracings of the ECG, LV pressure and LV-RA distance during VOO pacing of a dog heart, wherein intrinsic atrial contractions slowly advance in front of the paced QRS complex, thus demonstrating changes in the LV-RA distance signal that result from mitral valve opening (MVO) and atrial contraction (atrial kick)
Figure 15:
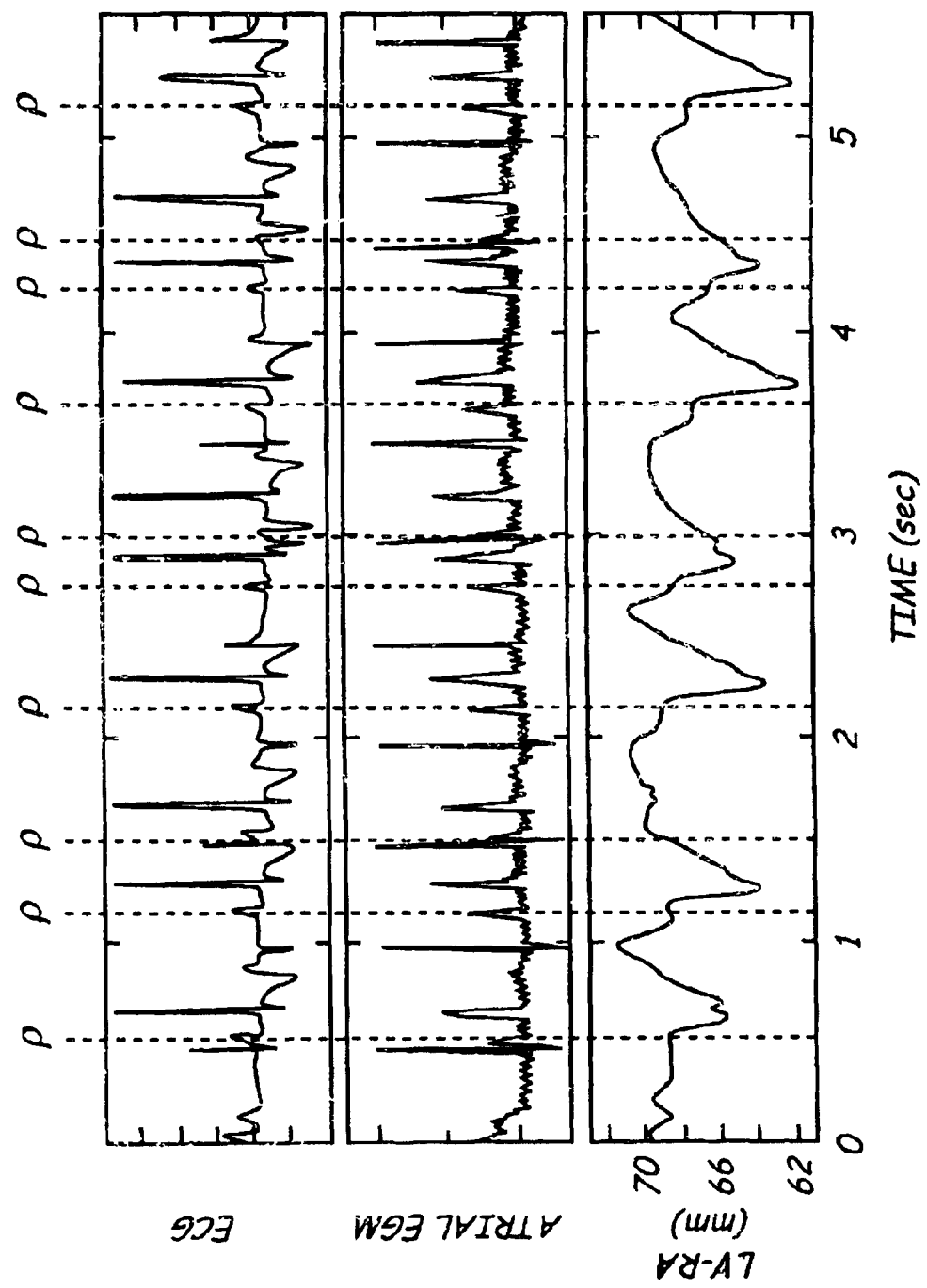
FIG. 15 illustrates signal tracings of the ECG, atrial EGM and the LV-RA distance from a dog heart illustrating the concept of "atrial efficacy" as assessed by the LV-RA distance which varies in magnitude as a function of the atrial filling time and status of the mitral and tricuspid valves.

The information contained in the LV-RA distance signal is described in FIG. 14. This data was obtained during VOO pacing in a dog. The intrinsic P waves advance from an ineffective position coincident with the QRS, to a more natural location in advance of the QRS. The LV-RA distance decreases slowly at the conclusion of ventricular systole, which reflects opening of the mitral and tricuspid valves (indicated by "MVO" in the figure), and drainage of the atria into the ventricles. A more rapid decrease in the LV-RA signal occurs immediately after atrial electrical systole. Finally, ventricular systole causes a small inflection in the LV-RA signal (indicated by "VC" in the figure). FIGS. 14 and 15 demonstrate how the LV-RA signal reports "atrial efficacy". In these figures, the contraction of the LV-RA signal immediately following a P wave reflects the mechanical efficacy of the atrial contraction. P-waves that occur in normal synchrony with ventricular systole, and that follow a sufficient filling time after the prior ventricular systole, result in a significant decrease in the LV-RA signal. Conversely, P-waves that occur during ventricular systole or after insufficient filling time cause little decrease in the LV-RA signal.

Figure 16:
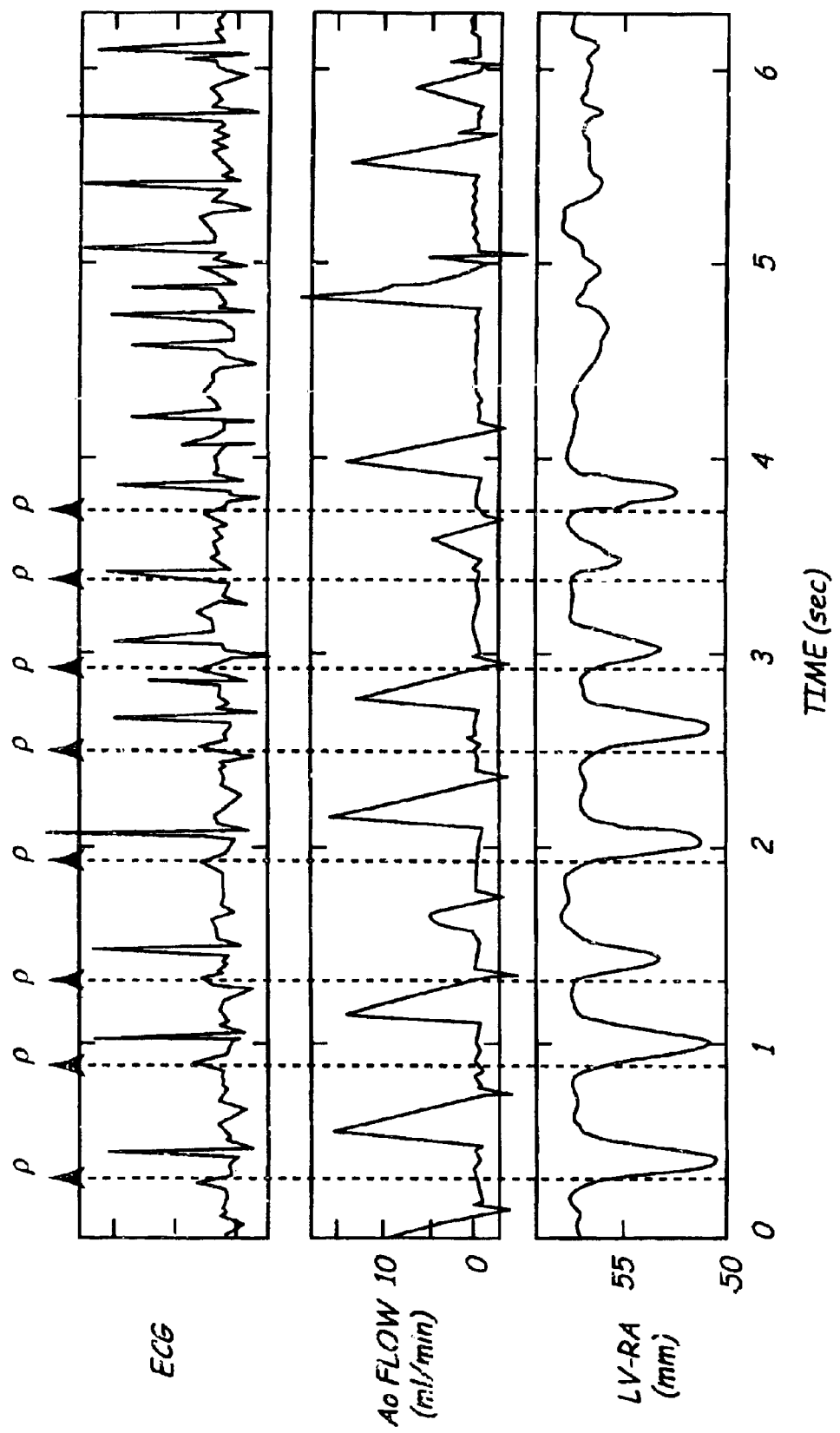
FIG. 16 illustrates signal tracings of he ECG, aortic blood flow and the LV-RA distance, wherein the loss of atrial mechanical function is evident in the change in the LV-LA distance following induction of atrial fibrillation in a dog heart.
Figure 17:
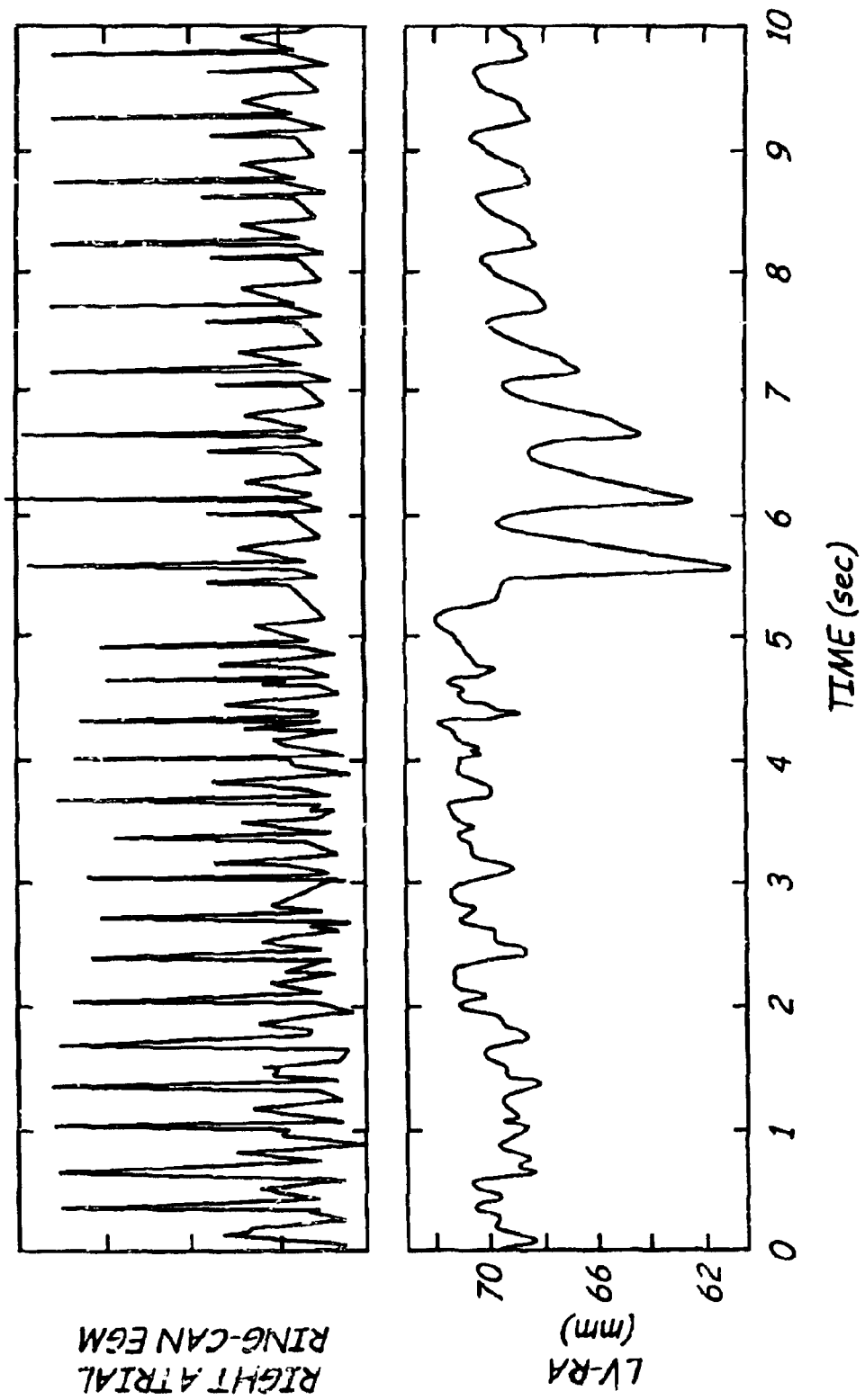
FIG. 17 illustrates signal tracings of a far-field atrial electrogram and the LV-RA distance during atrial fibrillation and spontaneous reversion to normal sinus rhythm in a dog heart.

FIGS. 16 and 17 show the changes in the LV-RA signal that result from atrial fibrillation. In FIG. 16, the induction of atrial fibrillation clearly decreases the atrial efficacy as assessed by the LV-RA signal. In FIG. 17, atrial efficacy is markedly improved immediately after spontaneous reversion from AF to normal sinus rhythm.

Figure 18:
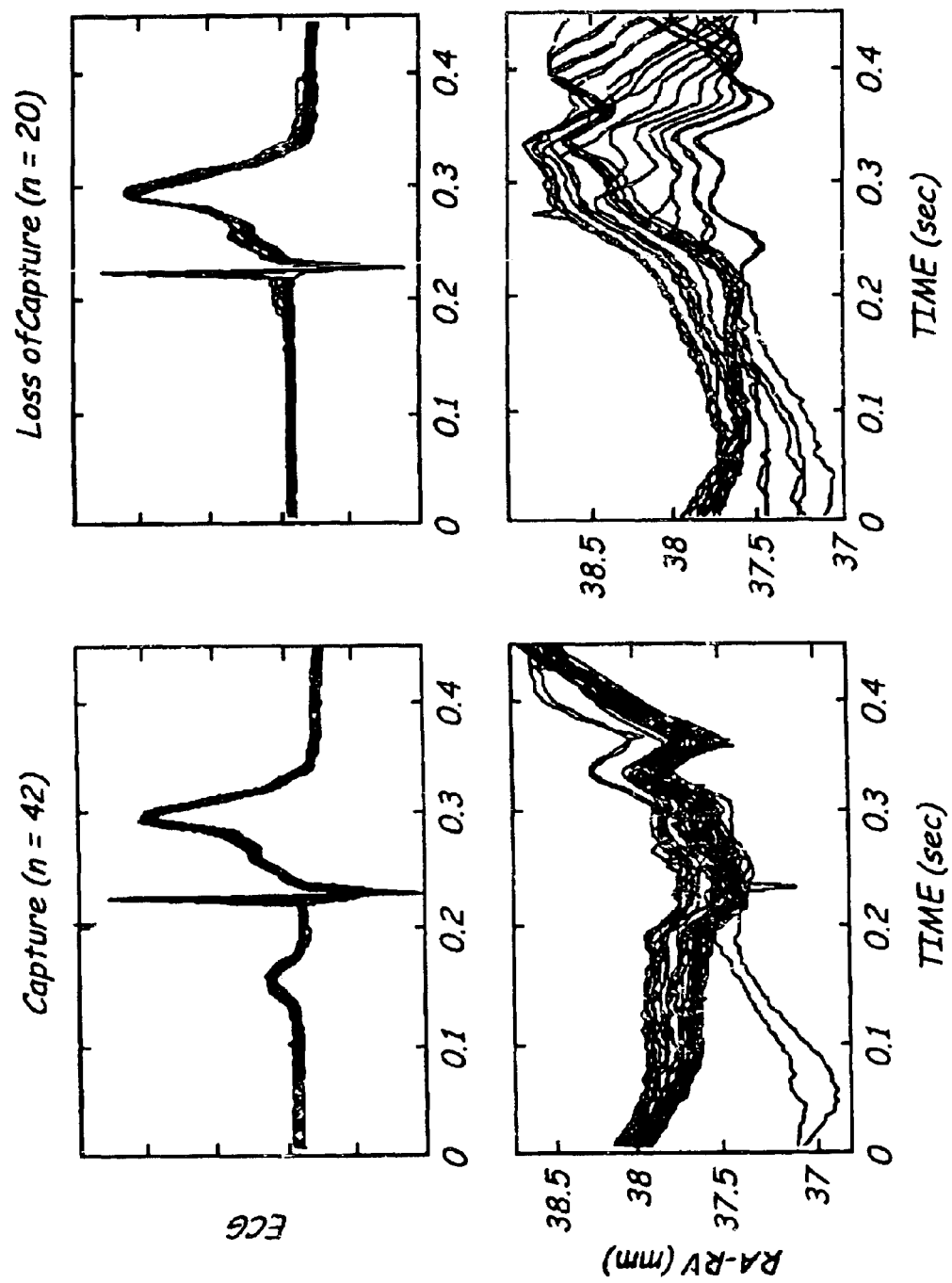
FIG. 18 illustrates signal tracings of the ECG and RA-RV distance signal during DOO pacing of a dog heart during atrial capture (left tracings) contrasted with loss of atrial capture (right tracings)
Figure 19:
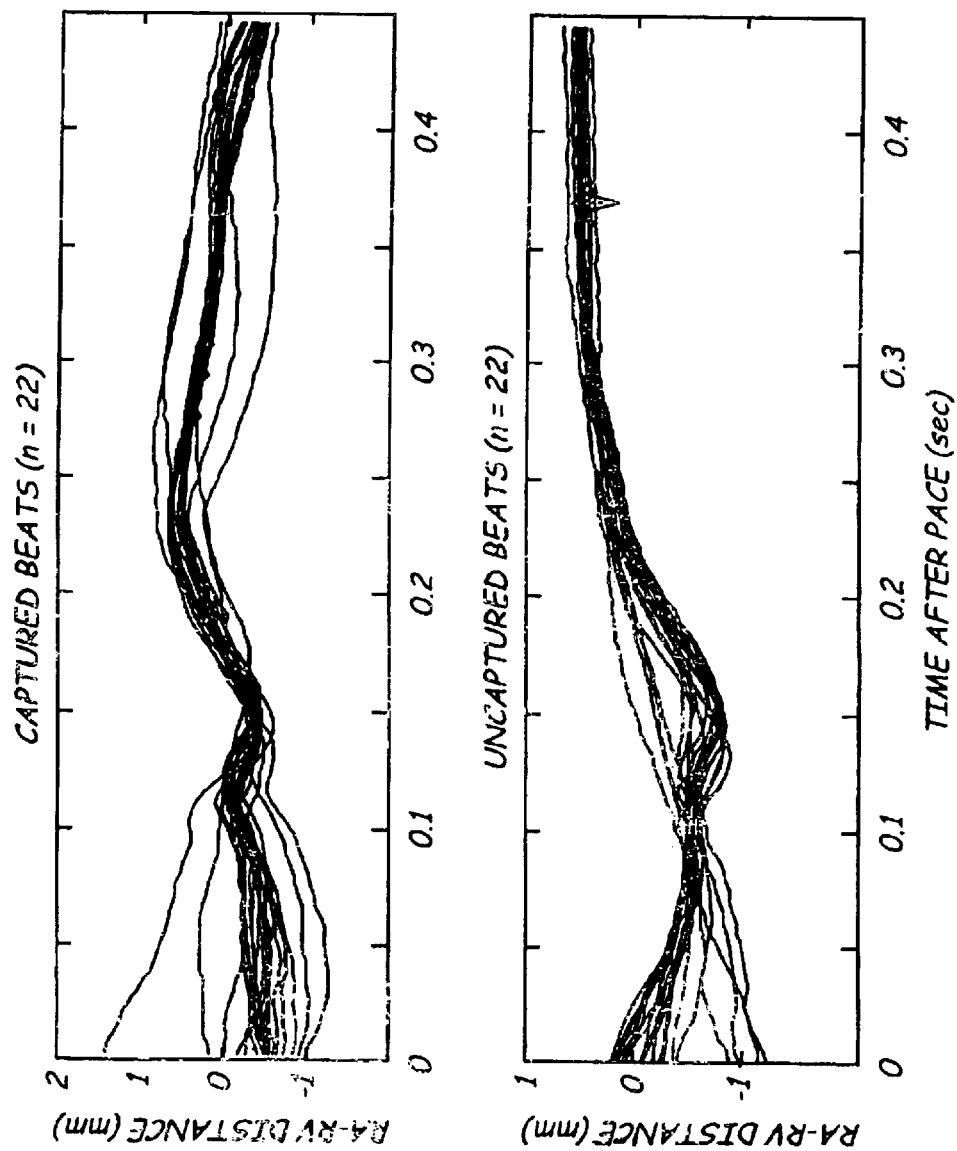
FIG. 19 illustrates signal tracings of the RA-RV distance signal during DOO pacing of a dog heart during ventricular capture (upper tracings) contrasted with loss of ventricular capture (lower tracings).

In contrast to the RV-LV and LV-RA signals, the RV-RA signal was very inconsistent in the 4 canines studied. FIG. 18 is an example of this inconsistency for dog 3 and dog 4. Although the RV-RA signals look similar, the timing of events in the two signals, relative to the ECG, is quite different. This disparity may be a result of varied crystal location in the right atrium, and careful crystal placement might lead to more consistent results. FIG. 19 shows the difference in RV-RA signal for DOO pacing with and without atrial capture. In this example, the RV-RA signal during atrial loss of capture is distinct from that of atrial capture, except for cases where intrinsic atrial activation occurs near the nominal location. Finally, FIG. 20 shows the difference in RV-RA signal for DOO pacing with and without ventricular capture.

In summary, this pilot study was conducted to demonstrate feasibility of lead-based sonomicrometry measurements of intracardiac distances, and to describe the information content of distance measurements between three pacing lead locations: the RV apex, the RA appendage, and the CS. The sonomicrometer measurements of distance and motion were accurate when compared with caliper and fluoroscopic distance measurements. The distance between the CS and RV crystals consistently decreased during-shaped LV ejection. LV stroke volume was estimated from the systolic shortening of the RV-LV distance with a standard deviation of 1 to 1.5 ml in 4 dogs. However, this estimator of stroke volume was sensitive to crystal location and changes in LV dynamics. The systolic rate of shortening of the RV-LV distance was highly correlated with the maximum dP/dt in the LV (which is generally accepted as an index of cardiac contractility). Decreases in the LV-RA distance occurred during atrial contraction, and often designated the opening of the mitral/tricuspid valves. Finally, the morphology of the RV-RA distance signal was relatively inconsistent between canines.

Particular Applications to IMDs:

Returning to the IMD depicted in FIGS. 1–3, the system and method of the present invention is advantageously employed to measure cardiac dimensions in real time and to either record or transmit these values for monitoring purposes. Or, the system and method can use these values as feedback to modify the delivery of electrical or pharmacological therapy, particularly in the treatment of heart failure using multi-chamber pacing regimens and in controlling other pacing and cardioversion/defibrillation functions. There are many possible applications of the method and system of the present invention, including but not limited to:

Multi-site Pacing of Heart Failure Patients:

A number of proposals have been advanced for providing pacing therapies to alleviate heart failure conditions and restore synchronous depolarization and contraction of a single heart chamber or right and left, upper and lower, heart chambers as described in detail in commonly assigned U.S. Pat. Nos. 5,403,356, 5,797,970, 5,902,324, 6,219,579, 6,223,082, and 6,070,100, and in U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", PACE (Vol. 16, Part II, NASPE Abstract 141, p.885, April 1993); Daubert et al., "Permanent Left Ventricular Pacing With Transvenous Leads Inserted Into The Coronary Veins", PACE (Vol. 19, Part II, pp. 239–245, January 1998); Cazeau et al., "Four Chamber Pacing in Dilated Cardiomyopathy", PACE (Vol. 17, Part II, pp. 1974–1979, November 1994); and Daubert et al., "Renewal of Permanent Left Atrial Pacing via the Coronary Sinus", PACE (Vol. 15, Part II, NASPE Abstract 255, p. 572, April 1992).

In most cases, it has been proposed that bi-ventricular pacing pulses be applied simultaneously to the right and left ventricles. An observation is made in commonly assigned U.S. Pat. No. 6,219,579 that the exact timing of mechanical events are important for properly controlling right and left heart chamber pacing so as to optimize left ventricular output. Specifically, it is known that actual contraction of one ventricular chamber before the other has the effect of moving the septum so as to impair full contraction in the later activated chamber. Thus, while concurrent or simultaneous pacing of the left and right ventricle may achieve a significant improvement for CHF patients, it is better to provide for pacing of the two ventricles in such a manner that the actual mechanical contraction of the left ventricle, with the consequent closing of the valve, occurs in a desired time relationship with respect to the mechanical contraction of the right ventricle and closing of the right value. For example, if conduction paths in the left ventricle are impaired, delivering a pacing stimulus to the left ventricle at precisely the same time as to the right ventricle may nonetheless result in left ventricular contraction being slightly delayed with respect to the right ventricular contraction.

In the above-referenced '324 patent, an AV synchronous pacing system is disclosed providing three or four heart chamber pacing through pace/sense electrodes located in or adjacent one or both of the right and left atrial heart chambers and in or adjacent to the right and left ventricular heart chambers. During an AV delay and during a V-A escape interval, a non-refractory ventricular sense event detected at either the right or left ventricular pace/sense electrodes starts a programmable conduction delay window (CDW) timer. A ventricular pace pulse is delivered to the other of the left or right ventricular pace/sense electrodes at the time-out of the CDW if a ventricular sense event is not detected at that site while the CDW times out. However, it is not always easy to determine just how to program the CDW duration to optimize the hemodynamics of the heart. As a consequence, it is important to provide a technique for measurement of mechanical events, such as a mechanical closure point of each of the ventricles, so as to be able to accurately program the sequence of pacing to achieve the desired dual ventricular pacing which optimizes ejection fraction, or cardiac output, for the individual patient.

The system of FIGS. 1–3 can be operated as a two-chamber, three-chamber or four-chamber pacing system providing synchronized RV and LV pacing in the manners described in the above-cited '324 patent or '100 patent. For example, the multi-site, AV sequential, bi-ventricular cardiac pacing system described above is selectively programmable to provide ventricular pacing pulses delivered to one or both of the RV and LV sites synchronously within a V-V delay following time-out of an AV delay from a preceding delivered atrial pace (A-PACE) pulse or an atrial sense (A-EVENT), typically, the RA-PACE pulse or the RA-EVENT, and operating in accordance with the steps of: (a) timing an AV delay from a preceding delivered A-PACE pulse or A-EVENT; (b) detecting a V-SENSE at one of a first and second ventricular site within the AV delay and, in response, terminating the AV delay and providing a V-EVENT; (c) delivering a V-PACE1 pulse to a selected one of the first and second ventricular sites upon the time-out of the AV delay or, in a triggered mode, upon the V-SENSE; (d) timing a V-V delay comprising one of a VS-VP pace delay from a V-EVENT occurring prior to the time-out of the AV delay or a VP-VP pace delay from the V-PACE1 delivered at the end of the AV delay or a VS/VP-VP pace delay from a triggered V-PACE1; and (e) delivering a V-PACE2 pulse to the other of the first and second ventricular sites upon the time-out of the V-V delay.

The optimal timing of atrial and ventricular pacing, or the optimal timing of multi-site ventricular pacing cannot be determined from electrical activity alone. The quantitative hemodynamic information produced by the method and apparatus of the present invention would enable optimal timing of delivery of pacing pulses to the heart chambers by optimally adjusting the operative AV delays, V-V pacing delays for bi-ventricular pacing and CDWs, if employed, to obtain a maximal value of a weighted combination of the systolic shortening of the RV-LV distance value D1 and the inverse of the end diastolic distance for a given heart rate.

Such a multi-site pacing IMD functions from the time of implantation and initial programming and baseline parameter measurements through successive cycles of gathering parameter data in the IMD, uplink telemetry transmission of the accumulated data to an external programmer, for display and analysis, leading to possible reprogramming and baseline parameter measurement to better assess the heart failure state. Optionally, the pacing parameters, particularly the AV delays following an A-PACE (PAV delay) or an A-EVENT (SAV delay), can be adjusted and the optimal LV function determined from time to time when specific measurement and adjustment criteria are met.

Periodically, the RV-LV distance D1 values are measured over one or more heart cycle and stored in IMD memory when an event trigger for initiating a session to derive the specific parameter occurs. The event criteria may be a programmed time or multiple times of every day or specified days of the week or month or the detection of the patient initiated parameter measurement or some other programmed event, e.g., a combination of the time or times of day and a level of patient exercise indicated by the activity signal processor circuit. Typically, the measurement of the LV distance data should take place when the heart rate is in a normal range and is stable within a certain stability tolerance which can both be programmed by the physician and are determined over a series of heart cycles in a manner well known in the art.

In addition, an algorithm to adjust the V-V delay and/or SAV delay and/or PAV delay or other pacing parameters to provide measured RV-LV dimension D1 data values can be entered and performed. The V-V delay and/or SAV delay and/or PAV delay or other pacing parameters that provides the optimal RV-LV dimension D1 value is then selected to control pacing until the event criteria are next met and they are found to differ in any respect.

The physician can also enter programming commands that enable successive changes in each of the SAV delay, PAV delay and V-V delay to be tested. In many clinical cases, only the optimal V-V delay in the RV-LV or LV-RV sequence would be obtained. In other clinical cases, the optimal SAV delay would be first obtained, and then the optimal V-V delay in the RV-LV or LV-RV sequence would be obtained. In certain clinical cases, the PAV delay would be automatically set to be the same as the optimal SAV delay. The order of the process and the tests included in the process can be left to the clinicians to develop for the particular patient.

Confirmation of Malignant Tachyarrhythmia:

Current ICDs and other anti-tachyarrhythmia control devices analyze the intrinsic atrial and/or ventricular heart rate, rate stability and/or EGM morphology to determine over a number of heart cycles whether a high intrinsic atrial or ventricular heart rate is sinus in nature, and not harmful, or malignant and requiring delivery of a burst stimulation or cardioversion/defibrillation shock therapy. Diminished shortening of either the RV-LV distance D1 and/or RV-RA distance D3 during systole can be employed to verify a provisional determination of a malignant tachyarrhythmia in the ventricles. Alternately, if a ventricular arrhythmia is detected by analysis of the intrinsic atrial and ventricular heart rate, rate stability, and/or EGM morphology, the measurement of systolic shortening of either the RV-LV distance D1 and/or the RV-RA distance D3 can be used to gauge the urgency for terminating the arrhythmia. Arrhythmias with larger systolic shortening of D1 or D3 may be hemodynamically stable, thus allowing time for several burst stimulation attempts at termination. Arrhythmias with small systolic shortening of D1 or D3 may be hemodynamically unstable and should be treated immediately with cardioversion/defibrillation shock therapy.

Moreover, the strength of contractions of the arrhythmic heart chamber can be determined as a function of the measured distances, and the selection and delivery of either burst anti-tachycardia pacing or an electrical cardioversion/defibrillation shock can be made depending on the strength of contractions of the heart chamber.

Detection of Electromechanical Dissociation During Pacing or Arrhythmias:

At times, especially after delivery of an anti-tachyarrhythmia therapy to terminate a malignant tachyarrhythmia, the electrical activity of the atria and ventricles indicate slow heart rhythm yet the mechanical pumping action of the heart is absent or greatly impaired. Thus, the heart function is not fully restored although the termination of tachyarrhythmia is determined by the IMD from the normal sense event signals that do not satisfy tachyarrhythmia detection criteria that would, if satisfied, indicate failure of the anti-tachyarrhythmia therapy or resumption of the tachyarrhythmia. This condition, referred to as pulse less electrical activity (PEA), can be detected by normal electrical sensing of the IMD but diminished mechanical contraction as sensed by the measured distances D1 or D3. In this situation, alternative forms of electrical stimulation of the myocardium may be beneficial.

Therefore, an appropriate one of the sonomicrometer crystals 70, 72 and 74 is energized, and the appropriate one of the distance measurements D1, D2 and D3 are obtained over a time period following delivery of a cardioversion/defibrillation therapy to a heart chamber, to determine that the heart chamber is functioning mechanically. The efficacy of the delivered anti-tachyarrhythmia therapy can be determined and mistaken reliance on electrical activity in a PEA state can be avoided.

Mechanical Confirmation of Capture:

The thresholds for pacing stimuli are difficult to determine from electrical activity alone. Minimization of the energy of pacing stimuli is useful for increasing battery longevity, but if pacing stimuli are too small, patient safety is jeopardized. The method and apparatus of the present invention would provide proof of mechanical contraction of the heart in response to a pacing stimulus, thereby facilitating safe minimization of pacing energy.

In general, in FIGS. 1–3, a pacing pulse is delivered to any the RA, RV, LA and LV pace/sense electrode pairs to elicit a contraction of the respective heart chamber. An appropriate one of the sonomicrometer crystals 70, 72 and 74 is energized, and the distance measurements are obtained over the time following delivery of the pacing pulse to measure the distance changes that would occur if the pacing pulse captures the heart chamber and causes a contraction. If the measured distance data indicates that the pacing pulse energy captured the heart chamber, then, the pacing pulse energy of succeeding pacing pulses could be decremented to reduce pacing pulse energy. If a contraction is not indicated by the measured distance data, then an appropriate response would be instituted, e.g., incrementally increasing the pacing energy of succeeding delivered pacing pulses and repeating the above steps until the pulse energy is sufficient to elicit the contraction of the heart chamber upon delivery of each pacing pulse. A high energy back-up pacing pulse could also be delivered each time that the pacing pulse fails to capture the heart. Usually, the determination of the pacing threshold sufficient to capture the heart is done periodically, and pacing pulse energy is set to the determined threshold energy plus a safety margin energy increment and remains constant between periodic determinations of the capture threshold.

Chronic Monitoring of Contractility and Cardiac Output:

Cardiac output is perhaps the most important overall parameter of cardiac performance, but it is difficult to measure acutely, and has never been measured chronically in humans. The method and apparatus of the present invention would provide a chronic surrogate measurement of cardiac output, which could greatly enhance the patients overall medical care. A relative measure of changes in cardiac output over time would be obtained by measuring the systolic shortening of the LV-RV distance D1, multiplied by the current heart rate. An absolute measure of cardiac output would require the physician to first establish the relationship between stroke volume and the systolic shortening of the LV-RV distance D1, such as shown in FIG. 10. The stroke volume measurement could be obtained for example by transthoracic ultrasound as is well known in the art.

A second important parameter of cardiac performance is the cardiac contractility. As shown in FIG. 13, there is a strong correlation between the measured rate of systolic shortening of the LV-RV distance D1 and the maximum change in LV pressure during systole (dP/dT), an established measurement of cardiac contractility. Therefore, the measured rate of systolic shortening of the LV-RV distance D1 can serve as a surrogate measurement of cardiac contractility.

Rate Responsive Pacing:

Delivering a pacing therapy that includes physiological changes in heart rate is a longstanding problem. The method and apparatus of the present invention can measure cardiac contractility, which can be used to modulate heart rate.

In FIG. 2, the pacing rate determined by micro-computer-based timing and control system 102 can be programmed to develop a pacing rate from rate control parameters including the activity signal generated by activity signal processor circuit 118 and the determined cardiac contractility. The determination of the pacing rate can be dependent upon the determined contractility alone or in combination with the activity signal following a variety of algorithms well known in the art.

Automatic Adjustment of Sense Amplifier Sensitivity:

IMDs that sense the electrical activity of the heart usually include thresholds for separating electrical noise from cardiac events. These thresholds are often manually adjusted by the physician after implant and during follow-up visits. The method and apparatus of the present invention could provide the necessary feedback for automated adjustment of sense amplifier sensitivity, by reporting mechanical contractions which should be detected by the sense amplifier.

In FIGS. 2 and 3, the sense amplifiers in the input signal processing circuit 108 are adjustable in sensitivity by an appropriate timing and control signal to sense electrical activity across the RA, LA, RV and LV pace/sense electrode pairs in the pacing system so as to only sense signals of interest in that heart chamber and provide a sense event signal while avoiding oversensing of noise or electrical signals originating in the other heart chambers. An appropriate one of the sonomicrometer crystals 70, 72 and 74 is energized, and the distance measurements are obtained over the cardiac cycle following delivery of a pacing pulse to measure the distance changes that would occur if the pacing pulse captures the heart chamber and causes a contraction or that would occur when the heart chamber spontaneously contracts. If a spontaneous contraction is evidenced by the measured distance data that is not accompanied by a sense event signal output by the sense amplifier, then a sense event signal may be declared and the sensitivity of the sense amplifier is increased. Usually, the determination of the sensing threshold sufficient to accurately detect signals of interest and not sense other signals is done periodically, and the sensing threshold is set to the determined sensing threshold plus a sensitivity increment and remains constant between periodic determinations of the sensing threshold.

Detection of 2:1 Pacing:

As pacing rate increases, the heart often enters a state where every other paced beat does not result in mechanical contraction. This results in an instantaneous reduction of heart rate by 50%, and great discomfort to the patient. The method and apparatus of the present invention could be used to detect the absence of every other mechanical contraction that should follow delivery of each paced event and adjust pacing rate to a rate where 2:1 pacing no longer occurs.

In general, in FIGS. 1–3, a pacing pulse is delivered to any the RA, RV, LA and LV pace/sense electrode pairs to elicit a contraction of the respective heart chamber. An appropriate one of the sonomicrometer crystals 70, 72 and 74 is energized, and the distance measurements are obtained over the time following delivery of the pacing pulse to measure the distance changes that would occur if the pacing pulse captures the heart chamber and causes a contraction. If a contraction is not indicated by the measured distance data, then an appropriate response would be instituted, e.g., the above-described stimulation threshold determination. If the increased pacing energy does not solve the loss of capture, if a 2:1 loss of capture pattern is evident, and if pacing rate is elevated above the lower rate limit, then the pacing rate of succeeding delivered pacing pulses can be decreased to a rate where the 2:1 pattern is no longer evident.

Appropriate Pacemaker Mode Switching:

Pacemakers are often programmed to deliver ventricular pacing synchronously with observed intrinsic atrial activity. This can cause hemodynamic instability when atrial arrhythmias develop. Modern pacemakers attempt to detect changes in atrial activity consistent with atrial arrhythmias, and automatically convert to a pacing mode in which ventricular activity does not track atrial activity. The method and apparatus of the present invention could directly detect the ventricular hemodynamic changes that call for a mode switch.

Monitoring Atrial Mechanical Function:

Because of the small muscle mass of the atria relative to the ventricles, atrial electrical activity is of much lower amplitude than ventricular electrical activity. The atrial electrical activity is often difficult to detect, and the neighboring ventricular electrical activity can often be mistakenly detected in the atrial electrogram, causing false sensing or oversensing. The method and apparatus of the present invention could be used to monitor atrial mechanical electrical activity, to detect the presence of arrhythmias or ineffective atrial contraction (i.e., contraction against a closed tricuspid or mitral valve), and to reject the erroneously sensed ventricular electrical activity.

In FIGS. 2 and 3, an appropriate one of the sonomicrometer crystals 70, 72 and 74 or 74' is energized periodically over the heart cycle, and the distance D2 and/or D3 or D4 measurement is obtained. The mechanical contraction of the RA or LA is determined from the changes in the distance D2 and/or D3 or D4 and correlated to the output of the RA or LA sense amplifier. If an atrial contraction is not indicated by the measured distance data, then the RA or LA sense event signal is ignored, and RA or LA sense amp sensitivity can be adjusted as described above to attempt to minimize oversensing. Conversely, it may be appropriate to declare an RA or LA sense event from the distance measurement and eliminate reliance upon the RA or LA sense amplifier.

Prediction of Syncope:

Early prediction of syncope could lead to the application of preventative therapy. Reduction of cardiac output or other changes in mechanical activity or size of the heart may precede syncope and could be used to time the delivery of preventative therapy.

Summary:

It will be appreciated from the above description that the implanted monitor/stimulator of the present invention may be utilized to obtain the aforementioned parameters as stored patient data over a period of time. The treating physician is able to initiate uplink telemetry of the patient data in order to review it to make an assessment of the electrical and mechanical function of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, e.g., pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and of the therapies that are delivered.

All patents and publications referenced herein are hereby incorporated by reference in there entireties.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of cardiac monitors, pacing systems and ICDs that are not disclosed and are not necessary to the practice of the present invention. In addition, it will be understood that specifically described structures, functions and operations set forth in the above-incorporated patents and publications can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A method of operating an implantable medical device comprising a plurality of leads and an implantable medical device circuit enclosed within a hermetically sealed housing in relation to cardiac mechanical function of a first heart chamber during a heart cycle comprising:

implanting a first lead bearing a first sonomicrometer crystal at a first location of the heart outside the first heart chamber;

implanting a second lead bearing a second sonomicrometer crystal at a second location of the heart outside the first heart chamber, whereby the first and second locations define a vector across and through a substantial portion of the first heart chamber;

coupling the first and second leads to the implantable medical device circuit and implanting the housing in the patient, and operating the implantable medical device by:

during one or more heart cycle, periodically energizing one of the first and second sonomicrometer crystals to emit an ultrasonic frequency emitted signal that causes the other of the first and second sonomicrometer crystals to develop an ultrasonic frequency sense signal;

determining the distance between the first and second sonomicrometer crystals as a function of the time delay between emission of the emitted signal and sensing of the respective sense signal; and adjusting the operation of the implantable medical device as a function of the determined distances between the first and second sonomicrometer crystals during a heart cycle.

2. The method of claim 1, wherein the implantable medical device comprises an implantable pacing system, and further comprising:

delivering a pacing pulse to the first heart chamber to elicit a contraction of the first heart chamber;

and wherein the adjusting step comprises adjusting a parameter of the delivered pacing pulse as a function of the determined distance between the first and second sonomicrometer crystals during a heart cycle following delivery of a pacing pulse.

3. The method of claim 1, wherein the implantable medical device comprises an implantable pacing system, and further comprising:

delivering a pacing pulse to the first heart chamber to elicit a contraction of the first heart chamber; and wherein:

the determining step further comprises determining if a series of distances measured during the determining step represents a contraction of the first heart chamber; and the adjusting step comprises adjusting the pacing energy of succeeding delivered pacing pulses to a pulse energy sufficient to elicit the contraction of the first heart chamber upon delivery of each pacing pulse.

4. The method of claim 1, wherein the implantable medical device comprises an implantable pacing system, and further comprising:

delivering pacing pulses to the first heart chamber at a predetermined pacing rate to elicit contractions of the first heart chamber; and wherein:

the determining step further comprises determining if the distance measured during the determining step represents a contraction of the first heart chamber; and the adjusting step comprises adjusting the pacing rate of succeeding delivered pacing pulses to a pacing rate sufficient to elicit the contraction of the first heart chamber upon delivery of each pacing pulse.

5. The method of claim 1, wherein the implantable medical device comprises an implantable pacing system, and further comprising:

delivering pacing pulses to the first heart chamber at a predetermined pacing rate to elicit contractions of the first heart chamber; and wherein:

the determining step further comprises measuring the contractility of the first heart chamber as a function of the distances measured during the determining step; and the adjusting step comprises adjusting the pacing rate of succeeding delivered pacing pulses to a pacing rate that is proportional to the measured contractility sufficient to maximize the contractility of the first heart chamber upon delivery of each pacing pulse.

6. The method of claim 1, wherein the implantable medical device comprises an implantable pacing system, and further comprising:

operating a sense amplifier of the implantable pacing system to sense electrical activity of the first heart chamber accompanying a contraction of the first heart chamber and to provide a sense event signal; and wherein:

the determining step further comprises identifying a contraction of the first heart chamber as a function of the distances measured during the determining step; and the adjusting step comprises one of increasing the sensitivity of the sense amplifier or providing a sense event signal in the event that the sense amplifier does not provide a sense event signal when a contraction is identified as a function of the determined distance between the first and second sonomicrometer crystals during a heart cycle.

7. The method of claim 1, wherein the implantable medical device comprises an implantable pacing system, and further comprising:

operating a sense amplifier of the implantable pacing system to sense electrical activity of the first heart chamber accompanying a contraction of the first heart chamber and to provide a sense event signal; and wherein:

the determining step further comprises identifying a first heart chamber contraction of the first heart chamber as a function of the distances measured during the determining step; and the adjusting step comprises one of decreasing the sensitivity of the sense amplifier or ignoring the sense event signal in the event that the sense amplifier provides a sense event signal but a contraction is not identified as a function of the determined distance between the first and second sonomicrometer crystals during a heart cycle.

8. The method of claim 1, wherein the implantable medical device comprises an implantable pacing system, and further comprising:

delivering first and second pacing pulses separated in time by a pace delay to the first and second heart chambers, respectively, wherein the first and second heart chambers are right and left heart chambers, to elicit synchronized contractions of the first and second heart chambers; and wherein the adjusting step comprises adjusting the timing of delivery of the first and second pacing pulses as a function of the determined distances between the first and second sonomicrometer crystals during a heart cycle following delivery of first and second pacing pulses to maximize the value of a weighted combination of the systolic shortening of the RV-LV distance and the inverse of the end diastolic distance for a given heart rate.

9. The method of claim 1, wherein the implantable medical device comprises an implantable pacing system, and further comprising:

delivering a first pacing pulse to the left ventricle and a second pacing pulse to the right ventricle separated in time by a V-V pace delay to elicit synchronized contractions of the right and left ventricles; and wherein the adjusting step comprises adjusting the V-V pace delay as a function of the determined distance between the first and second sonomicrometer crystals to maximize the value of a weighted combination of the systolic shortening of the RV-LV distance and the inverse of the end diastolic distance for a given heart rate.

10. The method of claim 1, wherein the implantable medical device comprises an implantable pacing system, and further comprising:

delivering a first pacing pulse to the atria and a second pacing pulse to the ventricles separated in time by an AV delay to elicit synchronized contractions of the atria and ventricles; and wherein the adjusting step comprises adjusting the AV delay as a function of the determined distance between the first and second sonomicrometer crystals to maximize the value of a weighted combination of the systolic shortening of the RV-LV distance and the inverse of the end diastolic distance for a given heart rate.

11. The method of claim 1, wherein the implantable medical device comprises an anti-tachyarrhythmia control device for delivering a therapy in response to detection of a tachyarrhythmia of the first heart chamber, and the adjusting step comprises processing the determined distances to detect a tachyarrhythmia of the first heart chamber.

12. The method of claim 1, wherein the implantable medical device comprises an anti-tachyarrhythmia control device for delivering a therapy in response to detection of a tachyarrhythmia of the first heart chamber, and further comprising:

operating a sense amplifier of the implantable anti-tachyarrhythmia control device to sense electrical activity of the first heart chamber to provide sense event signals;

processing the sense event signals in relation to tachyarrhythmia detection criteria; and provisionally declaring a tachyarrhythmia state of the first heart chamber when the processed sense event signals satisfy tachyarrhythmia detection criteria;

and wherein:

the determining step further comprises determining the strength of contractions of the first heart chamber as a function of the distances measured during the determining step; and the adjusting step comprises confirming the tachyarrhythmia state in the event that the strength of contractions is decreased below a predetermined value.

13. The method of claim 1, wherein the implantable medical device comprises an anti-tachyarrhythmia control device for delivering a therapy in response to detection of a tachyarrhythmia of the first heart chamber, and further comprising:

operating a sense amplifier of the implantable anti-tachyarrhythmia control device to sense electrical activity of the first heart chamber to provide sense event signals;

processing the sense event signals in relation to tachyarrhythmia detection criteria; and declaring a tachyarrhythmia state of the first heart chamber when the processed sense event signals satisfy tachyarrhythmia detection criteria;

and wherein:

the determining step further comprises determining the strength of contractions of the first heart chamber as a function of the distances measured during the determining step; and the adjusting step comprises selection or delivery of either burst anti-tachycardia pacing or electrical cardioversion/defibrillation shock depending on the strength of contractions of the first heart chamber.

14. The method of claim 1, wherein the implantable medical device comprises an anti-tachyarrhythmia control device for delivering an anti-tachyarrhythmia therapy in response to detection of a tachyarrhythmia of the first heart chamber, and wherein:

the step of periodically energizing one of the first and second sonomicrometer crystals to emit an ultrasonic frequency emitted signal that causes the other of the first and second sonomicrometer crystals to develop an ultrasonic frequency sense signal is undertaken after delivery of an anti-tachyarrhythmia therapy;

the step of determining the distance between the first and second sonomicrometer crystals as a function of the time delay between emission of the emitted signal and sensing of the respective sense signal is undertaken after delivery of the anti-tachyarrhythmia therapy; and further comprising:

operating a sense amplifier of the implantable anti-tachyarrhythmia control device to sense electrical activity of the first heart chamber to provide sense event signals after delivery of the anti-tachyarrhythmia therapy; and determining the efficacy of the delivered anti-tachyarrhythmia therapy as a function of the determined distances between the first and second sonomicrometer crystals in the presence or absence of sense event signals, whereby one of successful termination of the tachyarrhythmia is determined, resumption of the tachyarrhythmia is determined requiring delivery of a further anti-tachyarrhythmia therapy is delivered, or pulse less electrical activity is determined, whereby a further electrical stimulation therapy is delivered to strengthen mechanical contraction of the first heart chamber.

15. A method of operating an implantable medical device in relation to cardiac mechanical function of a first heart chamber during a heart cycle comprising:

implanting a first lead bearing a first sonomicrometer crystal at a first location of the heart outside the first heart chamber;

implanting a second lead bearing a second sonomicrometer crystal at a second location of the heart outside the first heart chamber, whereby the first and second locations define a vector across and through a substantial portion of the first heart chamber; and coupling the first and second endocardial leads to an implantable medical device, and operating the implantable medical device by:

during one or more heart cycle, periodically energizing one of the first and second sonomicrometer crystals to emit an ultrasonic frequency emitted signal that causes the other of the first and second sonomicrometer crystals to develop an ultrasonic frequency sense signal;

determining the distance between the first and second sonomicrometer crystals as a function of the time delay between emission of the emitted signal and sensing of the respective sense signal; and deriving and storing data representing one or more of contractility and cardiac output of the first heart chamber from the determined distances in the implantable medical device.

16. The method of claim 15, wherein the implantable medical device comprises a therapy delivery system, and further comprising:

delivering a therapy to the first heart chamber as a function of one or more of contractility and cardiac output of the first heart chamber.

17. The method of claim 16, further comprising adjusting the operation of the implantable medical device as a function of the determined distances between the first and second sonomicrometer crystals during a heart cycle.

18. A method of operating an implantable medical device comprising a plurality of leads and an implantable medical device circuit enclosed within a hermetically sealed housing to determine dimensional changes or motion of a first heart chamber due to mechanical movement of the heart chamber during a heart cycle comprising:

implanting a first endocardial lead bearing a first sonomicrometer crystal through a venous pathway into a second heart chamber and disposing the first sonomicrometer crystal in association with the septum separating the first heart chamber from the second heart chamber, whereby the first sonomicrometer crystal is oriented toward but outside the first heart chamber;

implanting a second endocardial lead bearing a second sonomicrometer crystal through a venous pathway into a coronary vessel whereby the first and second sonomicrometer crystals are arranged in a vector extending through the first heart chamber;

coupling the first and second endocardial leads to the implantable medical device circuit, and operating the implantable medical device by:

during one or more heart cycle, periodically energizing one of the first and second sonomicrometer crystals to emit an ultrasonic frequency emitted signal that causes the other of the first and second sonomicrometer crystals to develop an ultrasonic frequency sense signal; and at each emission during the one or more heart cycle, determining the distance between the first and second sonomicrometer crystals as a function of the time delay between emission of the emitted signal and sensing of the respective sense signal, whereby the mechanical motion of the first heart chamber over the heart cycle can be determined without entering the first heart chamber including the wall of the first heart chamber.

19. The method of claim 17, further comprising adjusting the operation of the implantable medical device as a function of the determined distances between the first and second sonomicrometer crystals during a heart cycle.

20. The method of claim 18, wherein the implantable medical device comprises an implantable pacing system, and further comprising:

providing a first pace/sense electrode on the first endocardial lead adapted to be disposed in operative relation to the second heart chamber;

providing a second pace/sense electrode on the second endocardial lead adapted to be disposed in operative relation to the first heart chamber;

delivering a pacing pulse to one of the first and second heart chambers;

adjusting a parameter of the delivered pacing pulse as a function of the determined distances between the first and second sonomicrometer crystals during a heart cycle following delivery of the pacing pulse.

21. A method of determining dimensional changes in the left ventricle due to mechanical movement of the left ventricle during the heart cycle comprising:

implanting a first endocardial lead bearing a first sonomicrometer crystal through a venous pathway with the first sonomicrometer crystal lodged within the right ventricle separated from the left ventricle by the septal wall;

implanting a second endocardial lead bearing a second sonomicrometer crystal through a venous pathway through the right atrium and the ostium of the coronary sinus such that the second sonomicrometer crystal is lodged within a coronary vessel in relation to the left ventricle whereby the first and second sonomicrometer crystals are arranged in a vector through and across a substantial portion of the left ventricle;

during one or more heart cycle, periodically energizing one of the first and second sonomicrometer crystals to emit an ultrasonic frequency emitted signal that causes the other of the first and second sonomicrometer crystals to develop an ultrasonic frequency sense signal; and at each emission during the one or more heart cycle, determining the distance between the first and second sonomicrometer crystals as a function of the time delay between emission of the emitted signal and sensing of the respective sense signal, whereby the mechanical motion of the left ventricle over the heart cycle can be determined without entering the left ventricle.

22. The method of claim 21, further comprising the steps of:

implanting a third endocardial lead bearing a third sonomicrometer crystal through a venous pathway with the third sonomicrometer crystal is lodged in relation to one of the right atrium or the left atrium;

during one or more heart cycle, periodically energizing one of the first, second and third sonomicrometer crystals to emit an ultrasonic frequency emitted signal that causes the other two of the first, second, and third sonomicrometer crystals to develop ultrasonic frequency sense signals; and at each emission during the one or more heart cycle, determining the distance between the at least one of the first and second sonomicrometer crystals and the third sonomicrometer crystal as a function of the time delay between emission of the emitted signal and sensing of the respective sense signal, whereby the mechanical motion of the right atrium or the left atrium over the heart cycle can be determined.

23. A method of determining mechanical movement of the atria during the heart cycle comprising:

implanting a first endocardial lead bearing a first sonomicrometer crystal through a venous pathway with the first sonomicrometer crystal lodged within the right ventricle;

implanting a second endocardial lead bearing a second sonomicrometer crystal through a venous pathway with the second sonomicrometer crystal lodged in or along one of the left and right atrium, whereby the first and second sonomicrometer crystals are arranged in a vector through the one of the right and left atrium;

during one or more heart cycle, periodically energizing one of the first and second sonomicrometer crystals to emit an ultrasonic frequency emitted signal that causes the other of the first and second sonomicrometer crystals to develop an ultrasonic frequency sense signal; and at each emission during the one or more heart cycle, determining the distance between the first and second sonomicrometer crystals as a function of the time delay between emission of the emitted signal and sensing of the respective sense signal, whereby the mechanical motion of the atria can be determined.

24. A method of pacing the right and left ventricles to alleviate symptoms of heart failure comprising:

implanting a first lead bearing a first sonomicrometer crystal at a first location of the heart outside the left ventricle;

implanting a second lead bearing a second sonomicrometer crystal at a second location of the heart outside the left ventricle, whereby the first and second locations define a vector across and through a substantial portion of the left ventricle; and coupling an implantable medical device to the first and second leads, and operating the implantable medical device by:

repetitively timing a pacing escape interval establishing paced heart cycles:

delivering a first pacing pulse to one of the right and left ventricles at the time-out of each pacing escape interval and a second pacing pulse to the other of the right and left ventricles separated in time from the first pacing pulse by a pace delay;

during one or more heart cycle, periodically energizing one of the first and second sonomicrometer crystals to emit an ultrasonic frequency emitted signal that causes the other of the first and second sonomicrometer crystals to develop an ultrasonic frequency sense signal;

at each emission during the one or more heart cycle, determining the distance between the first and second sonomicrometer crystals as a function of the time delay between emission of the emitted signal and sensing of the respective sense signal, whereby the mechanical motion of the left ventricle over the heart cycle and cardiac output from the left ventricle can be assessed without entering the left ventricle; and adjusting the pace delay to maximize the assessed cardiac output.

25. The method of claim 24, wherein:

the implanting steps further comprise:

implanting a first endocardial lead bearing a first sonomicrometer crystal and a first pace/sense electrode through a venous pathway with the first sonomicrometer crystal lodged within the right ventricle separated from the left ventricle by the septal wall and the first pace/sense electrode situated for pacing the right ventricle; and implanting a second endocardial lead bearing a second sonomicrometer crystal and a second pace/sense electrode through a venous pathway through the right atrium and the ostium of the coronary sinus such that the second sonomicrometer crystal is lodged within a coronary vessel in relation to the left ventricle whereby the first and second sonomicrometer crystals are arranged in a vector through and across a substantial portion of the left ventricle and the second pace/sense electrode is situated for pacing the left ventricle; and the delivering step comprises delivering a right ventricular pacing pulse through the first pace/sense electrode and a left ventricular pacing pulse through the second pace/sense electrode.

26. The method of claim 25 further comprising:

implanting a third endocardial lead bearing a third sonomicrometer crystal and a third pace/sense electrode through a venous pathway with the third sonomicrometer crystal lodged within the one of the right and left atria separated from the first and second sonomicrometer crystals and the third pace/sense electrode situated for pacing the one of the right and left atria; and operating the implantable medical device by:

timing the pacing escape interval as a successive V-A interval and AV delay;

delivering an atrial pace pulse through the third pace/sense electrode at the time-out of each V-A interval and the first and second pacing pulses at the time-out of the AV delay;

adjusting the AV delay to maximize the assessed cardiac output.

27. The method of claim 24, further comprising operating the implantable medical device by:

timing the pacing escape interval as a successive V-A interval and AV delay;

delivering an atrial pace pulse to one of the right and left atria at the time-out of each V-A interval and the first and second pacing pulses at the time-out of the AV delay; and adjusting the AV delay to maximize the assessed cardiac output.

28. An implantable medical device comprising a plurality of leads and an implantable medical device circuit enclosed within a hermetically sealed housing comprising:

a first lead bearing a first sonomicrometer crystal at a first location of the heart outside a first heart chamber and coupled to the implantable medical device circuit;

a second lead bearing a second sonomicrometer crystal at a second location of the heart outside the first heart chamber and coupled to the implantable medical device circuit, whereby the first and second locations define a vector across and through a substantial portion of the first heart chamber;

means operable during one or more heart cycle for periodically energizing one of the first and second sonomicrometer crystals to emit an ultrasonic frequency emitted signal that causes the other of the first and second sonomicrometer crystals to develop an ultrasonic frequency sense signal;

means for determining the distance between the first and second sonomicrometer crystals as a function of the time delay between emission of the emitted signal and sensing of the respective sense signal; and means for adjusting the operation of the implantable medical device as a function of the determined distances between the first and second sonomicrometer crystals during a heart cycle.

29. The implantable medical device of claim 28, wherein the implantable medical device comprises an implantable pacing system, and further comprising:

means for delivering a pacing pulse to the first heart chamber to elicit a contraction of the first heart chamber; and wherein the adjusting means comprises means for adjusting a parameter of the delivered pacing pulse as a function of the determined distance between the first and second sonomicrometer crystals during a heart cycle following delivery of a pacing pulse.

30. The implantable medical device of claim 28, wherein the implantable medical device comprises an implantable pacing system, and further comprising:

means for delivering a pacing pulse to the first heart chamber to elicit a contraction of the first heart chamber; and wherein:

the determining means further comprises means for determining if a series of distances measured during the determining step represents a contraction of the first heart chamber; and the adjusting means comprises means for adjusting the pacing energy of succeeding delivered pacing pulses to a pulse energy sufficient to elicit the contraction of the first heart chamber upon delivery of each pacing pulse.

31. The implantable medical device of claim 28, wherein the implantable medical device comprises an implantable pacing system, and further comprising:

means for delivering pacing pulses to the first heart chamber at a predetermined pacing rate to elicit contractions of the first heart chamber; and wherein:

the determining means further comprises means for determining if the distance measured during the determining step represents a contraction of the first heart chamber; and the adjusting means further comprises means for adjusting the pacing rate of succeeding delivered pacing pulses to a pacing rate sufficient to elicit the contraction of the first heart chamber upon delivery of each pacing pulse.

32. The implantable medical device of claim 28, wherein the implantable medical device comprises an implantable pacing system, and further comprising:

means for delivering pacing pulses to the first heart chamber at a predetermined pacing rate to elicit contractions of the first heart chamber; and wherein:

the determining means further comprises means for measuring the contractility of the first heart chamber as a function of the distances measured during the determining step; and the adjusting means further comprises means for adjusting the pacing rate of succeeding delivered pacing pulses to a pacing rate that is proportional to the measured contractility sufficient to maximize the contractility of the first heart chamber upon delivery of each pacing pulse.

33. The implantable medical device of claim 28, wherein the implantable medical device comprises an implantable pacing system, and further comprising:

means for operating a sense amplifier of the implantable pacing system to sense electrical activity of the first heart chamber accompanying a contraction of the first heart chamber and to provide a sense event signal; and wherein:

the determining means further comprises means for identifying a contraction of the first heart chamber as a function of the distances measured during the determining step; and the adjusting means further comprises means for one of increasing the sensitivity of the sense amplifier or providing a sense event signal in the event that the sense amplifier does not provide a sense event signal when a contraction is identified as a function of the determined distance between the first and second sonomicrometer crystals during a heart cycle.

34. The implantable medical device of claim 28, wherein the implantable medical device comprises an implantable pacing system, and further comprising:

means for operating a sense amplifier of the implantable pacing system to sense electrical activity of the first heart chamber accompanying a contraction of the first heart chamber and to provide a sense event signal; and wherein:

the determining means further comprises means for identifying a first heart chamber contraction of the first heart chamber as a function of the distances measured during the determining step; and the adjusting means further comprises means for one of decreasing the sensitivity of the sense amplifier or ignoring the sense event signal in the event that the sense amplifier provides a sense event signal but a contraction is not identified as a function of the determined distance between the first and second sonomicrometer crystals during a heart cycle.

35. The implantable medical device of claim 28, wherein the implantable medical device comprises an implantable pacing system, and further comprising:

means for delivering first and second pacing pulses separated in time by a pace delay to the first and second heart chambers, respectively, wherein the first and second heart chambers are right and left heart chambers, to elicit synchronized contractions of the first and second heart chambers; and wherein the adjusting means further comprises means for adjusting the timing of delivery of the first and second pacing pulses as a function of the determined distances between the first and second sonomicrometer crystals during a heart cycle following delivery of first and second pacing pulses to maximize the value of a weighted combination of the systolic shortening of the RV-LV distance and the inverse of the end diastolic distance for a given heart rate.

36. The implantable medical device of claim 28, wherein the implantable medical device comprises an implantable pacing system, and further comprising:

means for delivering a first pacing pulse to the left ventricle and a second pacing pulse to the right ventricle separated in time by a V-V pace delay to elicit synchronized contractions of the right and left ventricles; and wherein the adjusting means further comprises means for adjusting the V-V pace delay as a function of the determined distance between the first and second sonomicrometer crystals to maximize the value of a weighted combination of the systolic shortening of the RV-LV distance and the inverse of the end diastolic distance for a given heart rate.

37. The implantable medical device of claim 28, wherein the implantable medical device comprises an implantable pacing system, and further comprising:

means for delivering a first pacing pulse to the atria and a second pacing pulse to the ventricles separated in time by an AV delay to elicit synchronized contractions of the atria and ventricles; and wherein the adjusting means further comprises means for adjusting the AV delay as a function of the determined distance between the first and second sonomicrometer crystals to maximize the value of a weighted combination of the systolic shortening of the RV-LV distance and the inverse of the end diastolic distance for a given heart rate.

38. The implantable medical device of claim 28, wherein the implantable medical device comprises an anti-tachyarrhythmia control device for delivering a therapy in response to detection of a tachyarrhythmia of the first heart chamber, and the adjusting means further comprises means for processing the determined distances to detect a tachyarrhythmia of the first heart chamber.

39. The implantable medical device of claim 28, wherein the implantable medical device comprises an anti-tachyarrhythmia control device for delivering a therapy in response to detection of a tachyarrhythmia of the first heart chamber, and further comprising:

means for operating a sense amplifier of the implantable anti-tachyarrhythmia control device to sense electrical activity of the first heart chamber to provide sense event signals;

means for processing the sense event signals in relation to tachyarrhythmia detection criteria; and means for provisionally declaring a tachyarrhythmia state of the first heart chamber when the processed sense event signals satisfy tachyarrhythmia detection criteria;

and wherein:
the determining means further comprises means for determining the strength of contractions of the first heart chamber as a function of the distances measured during the determining step; and
the adjusting means further comprises means for confirming the tachyarrhythmia state in the event that the strength of contractions is decreased below a predetermined value.

40. The implantable medical device of claim 28, wherein the implantable medical device comprises an anti-tachyarrhythmia control device for delivering a therapy in response to detection of a tachyarrhythmia of the first heart chamber, and further comprising:
means for operating a sense amplifier of the implantable anti-tachyarrhythmia control device to sense electrical activity of the first heart chamber to provide sense event signals;
means for processing the sense event signals in relation to tachyarrhythmia detection criteria; and
means for declaring a tachyarrhythmia state of the first heart chamber when the processed sense event signals satisfy tachyarrhythmia detection criteria;
and wherein:
the determining means further comprises means for determining the strength of contractions of the first heart chamber as a function of the distances measured during the determining step; and
the adjusting means further comprises means for selection or delivery of either burst anti-tachycardia pacing or electrical cardioversion/defibrillation shock depending on the strength of contractions of the first heart chamber.

41. The implantable medical device of claim 28, wherein the implantable medical device comprises an anti-tachyarrhythmia control device for delivering an anti-tachyarrhythmia therapy in response to detection of a tachyarrhythmia of the first heart chamber, and wherein:
the means for periodically energizing one of the first and second sonomicrometer crystals to emit an ultrasonic frequency emitted signal that causes the other of the first and second sonomicrometer crystals to develop an ultrasonic frequency sense signal is operated after delivery of an anti-tachyarrhythmia therapy;
the means for determining the distance between the first and second sonomicrometer crystals as a function of the time delay between emission of the emitted signal and sensing of the respective sense signal is operated after delivery of the anti-tachyarrhythmia therapy; and
further comprising:
means for operating a sense amplifier of the implantable anti-tachyarrhythmia control device to sense electrical activity of the first heart chamber to provide sense event signals after delivery of the anti-tachyarrhythmia therapy; and
means for determining the efficacy of the delivered anti-tachyarrhythmia therapy as a function of the determined distances between the first and second sonomicrometer crystals in the presence or absence of sense event signals, whereby one of successful termination of the tachyarrhythmia is determined, resumption of the tachyarrhythmia is determined requiring delivery of a further anti-tachyarrhythmia therapy is delivered, or pulse less electrical activity is determined, whereby a further electrical stimulation therapy is delivered to strengthen mechanical contraction of the first heart chamber.

42. An implantable medical device comprising a plurality of leads and an implantable medical device circuit enclosed within a hermetically sealed housing comprising:
a first lead bearing a first sonomicrometer crystal at a first location of the heart outside a first heart chamber and coupled to the implantable medical device circuit;
a second lead bearing a second sonomicrometer crystal at a second location of the heart outside the first heart chamber and coupled to the implantable medical device circuit, whereby the first and second locations define a vector across and through a substantial portion of the first heart chamber;
means operable during one or more heart cycle for periodically energizing one of the first and second sonomicrometer crystals to emit an ultrasonic frequency emitted signal that causes the other of the first and second sonomicrometer crystals to develop an ultrasonic frequency sense signal;
means for determining the distance between the first and second sonomicrometer crystals as a function of the time delay between emission of the emitted signal and sensing of the respective sense signal; and
means for deriving and storing data representing one or more of contractility and cardiac output of the first heart chamber from the determined distances in the implantable medical device.

43. The implantable medical device of claim 42, wherein the implantable medical device comprises a therapy delivery system, and further comprising:
means for delivering a therapy to the first heart chamber as a function of one or more of contractility and cardiac output of the first heart chamber.

44. The implantable medical device of claim 42, further comprising means for adjusting the operation of the implantable medical device as a function of the determined distances between the first and second sonomicrometer crystals during a heart cycle.

45. An implantable medical device comprising a plurality of leads and an implantable medical device circuit enclosed within a hermetically sealed housing comprising:
a first endocardial lead bearing a first sonomicrometer crystal disposed through a venous pathway into a second heart chamber in association with the septum separating the first heart chamber from the second heart chamber, whereby the first sonomicrometer crystal is oriented toward but outside the first heart chamber;
a second endocardial lead bearing a second sonomicrometer crystal disposed through a venous pathway into a coronary vessel alongside the first heart chamber whereby the first and second sonomicrometer crystals are arranged in a vector extending through the first heart chamber;
means operable during one or more heart cycle for periodically energizing one of the first and second sonomicrometer crystals to emit an ultrasonic frequency emitted signal that causes the other of the first and second sonomicrometer crystals to develop an ultrasonic frequency sense signal;
means for determining the distance between the first and second sonomicrometer crystals as a function of the time delay between emission of the emitted signal and sensing of the respective sense signal; and
means for deriving and storing data representing one or more of contractility and cardiac output of the first heart chamber from the determined distances in the implantable medical device.

46. The implantable medical device of claim 45, wherein the implantable medical device comprises a therapy delivery system, and further comprising:
  means for delivering a therapy to the first heart chamber as a function of one or more of contractility and cardiac output of the first heart chamber.

47. The implantable medical device of claim 45, further comprising means for adjusting the operation of the implantable medical device as a function of the determined distances between the first and second sonomicrometer crystals during a heart cycle.

48. The apparatus of claim 46, wherein the implantable medical device comprises an implantable pacing system, and further comprising:
  a first pace/sense electrode on the first endocardial lead adapted to be disposed in operative relation to the second heart chamber;
  a second pace/sense electrode on the second endocardial lead adapted to be disposed in operative relation to the first heart chamber;
  means for delivering a pacing pulse to one of the first and second heart chambers; and
  means for adjusting a parameter of the delivered pacing pulse as a function of the determined distances between the first and second sonomicrometer crystals during a heart cycle following delivery of the pacing pulse.

49. Apparatus for determining dimensional changes in the left ventricle due to mechanical movement of the left ventricle during the heart cycle comprising:
  a first endocardial lead bearing a first sonomicrometer crystal disposed through a venous pathway with the first sonomicrometer crystal lodged within the right ventricle separated from the left ventricle by the septal wall;
  a second endocardial lead bearing a second sonomicrometer crystal disposed through a venous pathway through the right atrium and the ostium of the coronary sinus such that the second sonomicrometer crystal is lodged within a coronary vessel in relation to the left ventricle, whereby the first and second sonomicrometer crystals are arranged in a vector through and across a substantial portion of the left ventricle;
  means for periodically energizing one of the first and second sonomicrometer crystals to emit an ultrasonic frequency emitted signal that causes the other of the first and second sonomicrometer crystals to develop an ultrasonic frequency sense signal; and
  means for determining the distance between the first and second sonomicrometer crystals as a function of the time delay between emission of the emitted signal and sensing of the respective sense signal, whereby the mechanical motion of the left ventricle over the heart cycle can be determined without entering the left ventricle.

50. The apparatus of claim 49, further comprising:
  a third endocardial lead bearing a third sonomicrometer crystal disposed through a venous pathway with the third sonomicrometer crystal is lodged in relation to one of the right atrium or the left atrium;
  means for periodically energizing one of the first, second and third sonomicrometer crystals to emit an ultrasonic frequency emitted signal that causes the other two of the first, second, and third sonomicrometer crystals to develop ultrasonic frequency sense signals; and
  means for determining the distance between the at least one of the first and second sonomicrometer crystals and the third sonomicrometer crystal as a function of the time delay between emission of the emitted signal and sensing of the respective sense signal, whereby the mechanical motion of the right atrium or the left atrium over the heart cycle can be determined.

51. Apparatus for determining dimensional changes of the atria comprising:
  a right ventricular endocardial lead bearing a first sonomicrometer crystal disposed through a venous pathway with the first sonomicrometer crystal lodged within the right ventricle;
  an atrial endocardial lead bearing a second sonomicrometer crystal disposed through a venous pathway with the second sonomicrometer crystal lodged in one of the right atrium or in the coronary sinus adjacent the left atrium, whereby the first and second sonomicrometer crystals are arranged in a vector through the one of the right and left atrium;
  means for periodically energizing one of the first and second sonomicrometer crystals to emit an ultrasonic frequency emitted signal that causes the other of the first and second sonomicrometer crystals to develop an ultrasonic frequency sense signal; and
  means for determining the distance between the first and second sonomicrometer crystals as a function of the time delay between emission of the emitted signal and sensing of the respective sense signal, whereby the mechanical motion of the atria can be determined.

52. Apparatus for pacing the right and left ventricles to alleviate symptoms of heart failure comprising:
  a first lead bearing a first sonomicrometer crystal disposed at a first location of the heart outside the left ventricle;
  a second lead bearing a second sonomicrometer crystal disposed at a second location of the heart outside the left ventricle, whereby the first and second locations define a vector across and through a substantial portion of the left ventricle;
  means for repetitively timing a pacing escape interval establishing paced heart cycles;
  means for delivering a first pacing pulse to one of the right and left ventricles at the time-out of each pacing escape interval and a second pacing pulse to the other of the right and left ventricles separated in time from the first pacing pulse by a pace delay;
  means for periodically energizing one of the first and second sonomicrometer crystals to emit an ultrasonic frequency emitted signal that causes the other of the first and second sonomicrometer crystals to develop an ultrasonic frequency sense signal;
  means for determining the distance between the first and second sonomicrometer crystals as a function of the time delay between emission of the emitted signal and sensing of the respective sense signal, whereby the mechanical motion of the left ventricle over the heart cycle and cardiac output from the left ventricle can be assessed without entering the left ventricle; and
  means for adjusting the pace delay to maximize the assessed cardiac output.

53. Apparatus for pacing the right and left ventricles to alleviate symptoms of heart failure comprising:
  a first endocardial lead bearing a first sonomicrometer crystal and a first pace/sense electrode disposed through a venous pathway with the first sonomicrometer crystal lodged within the right ventricle separated from the left ventricle by the septal wall and the first pace/sense electrode situated for pacing the right ventricle;

a second endocardial lead bearing a second sonomicrometer crystal and a second pace/sense electrode disposed through a venous pathway through the right atrium and the ostium of the coronary sinus such that the second sonomicrometer crystal is lodged within a coronary vessel in relation to the left ventricle whereby the first and second sonomicrometer crystals are arranged in a vector through and across a substantial portion of the left ventricle and the second pace/sense electrode is situated for pacing the left ventricle;

means for repetitively timing a pacing escape interval establishing paced heart cycles:

means for delivering a first pacing pulse through one of the first pace/sense electrode and the second pace/sense electrode at the time-out of each pacing escape interval and a second pacing pulse to the other of the first pace/sense electrode and the second pace/sense electrode separated in time from the first pacing pulse by a pace delay;

means for periodically energizing one of the first and second sonomicrometer crystals to emit an ultrasonic frequency emitted signal that causes the other of the first and second sonomicrometer crystals to develop an ultrasonic frequency sense signal;

means for determining the distance between the first and second sonomicrometer crystals as a function of the time delay between emission of the emitted signal and sensing of the respective sense signal, whereby the mechanical motion of the left ventricle over the heart cycle and cardiac output from the left ventricle can be assessed without entering the left ventricle; and means for adjusting the pace delay to maximize the assessed cardiac output of the left ventricle.

54. The apparatus of claim 53, further comprising:

a third endocardial lead bearing a third sonomicrometer crystal and a third pace/sense electrode disposed through a venous pathway with the third sonomicrometer crystal lodged within the one of the right and left atria separated from the first and second sonomicrometer crystals and the third pace/sense electrode situated for pacing the one of the right and left atria;

means for timing the pacing escape interval as a successive V-A interval and AV delay;

delivering an atrial pace pulse through the third pace/sense electrode at the time-out of each V-A interval and the first and second pacing pulses at the time-out of the AV delay; and adjusting the AV delay to maximize the assessed cardiac output.

55. An apparatus for use in providing therapy to a heart, comprising:

a sensor to measure at least one distance measurement in the heart;

a delivery circuit coupled to the sensor to deliver a first pacing pulse to a first location in the heart, to deliver a second pacing pulse to a second location in the heart, and to control time of delivery of at least one of the first and second pacing pulses based on the at least one distance measurement, wherein the sensor comprises:

a first sonomicrometer crystal disposed at a first location of the heart; and a second sonomicrometer crystal disposed at a second location of the heart, wherein the first and second sonomicrometer crystals are adapted for placement outside the left ventricle such that the first and second locations define a vector across a substantial portion of the left ventricle.

56. An apparatus for use in providing therapy to a heart, comprising:

a sensor to measure at least one distance measurement in the heart;

a delivery circuit coupled to the sensor to deliver a first pacing pulse to a first location in the heart, to deliver a second pacing pulse to a second location in the heart, and to control time of delivery of at least one of the first and second pacing pulses based on the at least one distance measurement, wherein the sensor comprises:

a first sonomicrometer crystal disposed at a first location of the heart; and a second sonomicrometer crystal disposed at a second location of the heart, and further comprising:

means to measure cardiac output of the heart; and wherein the delivery circuit includes a circuit to adjust the time of delivery of at least one of the first and second pacing pulses to maximize cardiac output.

* * * * *